US008461744B2

(12) United States Patent
Wiener et al.

(10) Patent No.: US 8,461,744 B2
(45) Date of Patent: Jun. 11, 2013

(54) ROTATING TRANSDUCER MOUNT FOR ULTRASONIC SURGICAL INSTRUMENTS

(75) Inventors: Eitan T. Wiener, Cincinnati, OH (US); Shan Wan, Mason, OH (US); Daniel W. Price, Loveland, OH (US); David K. Norvell, Monroe, OH (US); James R. Giordano, Milford, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 58 days.

(21) Appl. No.: 12/503,770

(22) Filed: Jul. 15, 2009

(65) Prior Publication Data
US 2011/0015660 A1    Jan. 20, 2011

(51) Int. Cl.
*H02N 2/00* (2006.01)

(52) U.S. Cl.
USPC ............ 310/323.01; 310/323.18; 310/323.19; 606/171

(58) Field of Classification Search
USPC    310/323.02, 323.12, 323.14, 323.17–323.19; 606/171
See application file for complete search history.

(56) References Cited

U.S. PATENT DOCUMENTS

| | | |
|---|---|---|
| 969,528 A | 9/1910 | Disbrow |
| 1,570,025 A | 1/1926 | Young |
| 2,704,333 A | 3/1955 | Calosi et al. |
| 2,736,960 A | 3/1956 | Armstrong |
| 2,849,788 A | 9/1958 | Creek |
| RE25,033 E | 8/1961 | Balamuth et al. |
| 3,015,961 A | 1/1962 | Roney |
| 3,513,848 A | 5/1970 | Winston et al. |
| 3,526,219 A | 9/1970 | Balamuth |
| 3,614,484 A * | 10/1971 | Shoh ............................ 310/325 |
| 3,636,943 A | 1/1972 | Balamuth |
| 3,776,238 A | 12/1973 | Peyman et al. |
| 3,805,787 A | 4/1974 | Banko |
| 3,830,098 A | 8/1974 | Antonevich |
| 3,854,737 A | 12/1974 | Gilliam, Sr. |
| 3,862,630 A | 1/1975 | Balamuth |
| 3,900,823 A | 8/1975 | Sokal et al. |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 4,156,187 A | 5/1979 | Murry et al. |
| 4,188,927 A | 2/1980 | Harris |

(Continued)

FOREIGN PATENT DOCUMENTS

| | | |
|---|---|---|
| CN | 1634601 A | 7/2005 |
| CN | 1640365 A | 7/2005 |

(Continued)

OTHER PUBLICATIONS

International Search Report for PCT/US2010/041663, Feb. 17, 2011 (8 pages).

(Continued)

*Primary Examiner* — Thomas Dougherty

(57) ABSTRACT

In one general aspect, various embodiments are directed to an ultrasonic surgical instrument that comprises a handpiece housing that operably supports an electrical contact assembly therein that is in electrical communication with a signal source. An acoustic assembly is supported within the handpiece housing in rotatable contact with the electrical contact assembly. In various embodiments, the signal source produces at least one of an ultrasonic signal and a radio frequency signal.

23 Claims, 15 Drawing Sheets

U.S. PATENT DOCUMENTS

| | | |
|---|---|---|
| 4,200,106 A | 4/1980 | Douvas et al. |
| 4,306,570 A | 12/1981 | Matthews |
| 4,445,063 A | 4/1984 | Smith |
| 4,491,132 A | 1/1985 | Aikins |
| 4,504,264 A | 3/1985 | Kelman |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,649,919 A | 3/1987 | Thimsen et al. |
| 4,708,127 A | 11/1987 | Abdelghani |
| 4,712,722 A | 12/1987 | Hood et al. |
| 4,827,911 A | 5/1989 | Broadwin et al. |
| 4,832,683 A | 5/1989 | Idemoto et al. |
| 4,838,853 A | 6/1989 | Parisi |
| 4,850,354 A | 7/1989 | McGurk-Burleson et al. |
| 4,865,159 A | 9/1989 | Jamison |
| 4,896,009 A | 1/1990 | Pawlowski |
| 4,903,696 A | 2/1990 | Stasz et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,026,387 A | 6/1991 | Thomas |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| 5,162,044 A | 11/1992 | Gahn et al. |
| 5,163,537 A | 11/1992 | Radev |
| 5,167,725 A | 12/1992 | Clark et al. |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| 5,213,569 A | 5/1993 | Davis |
| 5,221,282 A | 6/1993 | Wuchinich |
| 5,226,909 A | 7/1993 | Evans et al. |
| 5,226,910 A | 7/1993 | Kajiyama et al. |
| 5,241,236 A | 8/1993 | Sasaki et al. |
| 5,257,988 A | 11/1993 | L'Esperance, Jr. |
| 5,261,922 A | 11/1993 | Hood |
| 5,263,957 A | 11/1993 | Davison |
| 5,275,609 A | 1/1994 | Pingleton et al. |
| 5,282,800 A | 2/1994 | Foshee et al. |
| 5,304,115 A | 4/1994 | Pflueger et al. |
| D347,474 S | 5/1994 | Olson |
| 5,322,055 A | 6/1994 | Davison et al. |
| 5,324,299 A | 6/1994 | Davison et al. |
| 5,326,342 A | 7/1994 | Pflueger et al. |
| 5,344,420 A | 9/1994 | Hilal et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,366,466 A | 11/1994 | Christian et al. |
| 5,371,429 A | 12/1994 | Manna |
| D354,564 S | 1/1995 | Medema |
| 5,381,067 A | 1/1995 | Greenstein et al. |
| 5,403,312 A | 4/1995 | Yates et al. |
| 5,411,481 A | 5/1995 | Allen et al. |
| 5,419,761 A | 5/1995 | Narayanan et al. |
| 5,421,829 A | 6/1995 | Olichney et al. |
| 5,438,997 A | 8/1995 | Sieben et al. |
| 5,449,370 A | 9/1995 | Vaitekunas |
| 5,471,988 A | 12/1995 | Fujio et al. |
| 5,483,501 A | 1/1996 | Park et al. |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,562,609 A | 10/1996 | Brumbach |
| 5,562,610 A | 10/1996 | Brumbach |
| 5,601,601 A | 2/1997 | Tal et al. |
| 5,603,773 A | 2/1997 | Campbell |
| 5,607,436 A | 3/1997 | Pratt et al. |
| 5,618,492 A | 4/1997 | Auten et al. |
| 5,628,760 A | 5/1997 | Knoepfler |
| 5,630,420 A | 5/1997 | Vaitekunas |
| D381,077 S | 7/1997 | Hunt |
| 5,651,780 A | 7/1997 | Jackson et al. |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,730,752 A | 3/1998 | Alden et al. |
| 5,733,074 A * | 3/1998 | Stock et al. .................. 408/17 |
| 5,741,226 A | 4/1998 | Strukel et al. |
| 5,792,135 A | 8/1998 | Madhani et al. |
| 5,808,396 A | 9/1998 | Boukhny |
| 5,810,859 A | 9/1998 | DiMatteo et al. |
| 5,817,084 A | 10/1998 | Jensen |
| 5,817,119 A | 10/1998 | Klieman et al. |
| 5,827,323 A | 10/1998 | Klieman et al. |
| 5,828,160 A | 10/1998 | Sugishita |
| 5,836,897 A | 11/1998 | Sakurai et al. |
| 5,843,109 A | 12/1998 | Mehta et al. |
| 5,878,193 A | 3/1999 | Wang et al. |
| 5,879,364 A | 3/1999 | Bromfield et al. |
| 5,883,615 A | 3/1999 | Fago et al. |
| 5,893,835 A | 4/1999 | Witt et al. |
| 5,897,523 A | 4/1999 | Wright et al. |
| 5,897,569 A | 4/1999 | Kellogg et al. |
| 5,906,628 A | 5/1999 | Miyawaki et al. |
| 5,911,699 A | 6/1999 | Anis et al. |
| 5,935,143 A | 8/1999 | Hood |
| 5,935,144 A | 8/1999 | Estabrook |
| 5,938,633 A * | 8/1999 | Beaupre ........................ 604/22 |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,980,510 A * | 11/1999 | Tsonton et al. ................. 606/1 |
| 5,989,274 A | 11/1999 | Davison et al. |
| 5,989,275 A | 11/1999 | Estabrook et al. |
| 5,993,972 A | 11/1999 | Reich et al. |
| 6,024,741 A | 2/2000 | Williamson, IV et al. |
| 6,027,515 A | 2/2000 | Cimino |
| 6,033,375 A | 3/2000 | Brumbach |
| 6,050,943 A | 4/2000 | Slayton et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,132,368 A | 10/2000 | Cooper |
| 6,139,320 A | 10/2000 | Hahn |
| 6,139,561 A | 10/2000 | Shibata et al. |
| 6,142,615 A | 11/2000 | Qiu et al. |
| 6,147,560 A | 11/2000 | Erhage et al. |
| 6,152,902 A | 11/2000 | Christian et al. |
| 6,159,160 A | 12/2000 | Hsei et al. |
| 6,159,175 A | 12/2000 | Strukel et al. |
| 6,165,150 A | 12/2000 | Banko |
| 6,204,592 B1 * | 3/2001 | Hur ....................... 310/323.18 |
| 6,206,844 B1 | 3/2001 | Reichel et al. |

| Patent No. | Date | Inventor |
|---|---|---|
| 6,210,403 B1 | 4/2001 | Klicek |
| 6,214,023 B1 | 4/2001 | Whipple et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,252,110 B1 | 6/2001 | Uemura et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,340,352 B1 | 1/2002 | Okada et al. |
| 6,352,532 B1 | 3/2002 | Kramer et al. |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,387,109 B1 | 5/2002 | Davison et al. |
| 6,388,657 B1 | 5/2002 | Natoli |
| 6,391,042 B1 | 5/2002 | Cimino |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,561,983 B2 | 5/2003 | Cronin et al. |
| 6,572,632 B2 | 6/2003 | Zisterer et al. |
| 6,575,969 B1 | 6/2003 | Rittman, III et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,610,059 B1 | 8/2003 | West, Jr. |
| 6,616,450 B2 | 9/2003 | Mossle et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,656,177 B2 | 12/2003 | Truckai et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,676,660 B2 | 1/2004 | Wampler et al. |
| 6,678,621 B2 | 1/2004 | Wiener et al. |
| 6,679,899 B2 | 1/2004 | Wiener et al. |
| 6,682,544 B2 | 1/2004 | Mastri et al. |
| 6,689,146 B1 | 2/2004 | Himes |
| 6,716,215 B1 | 4/2004 | David et al. |
| 6,733,506 B1 | 5/2004 | McDevitt et al. |
| 6,770,072 B1 | 8/2004 | Truckai et al. |
| 6,773,443 B2 | 8/2004 | Truwit et al. |
| 6,773,444 B2 | 8/2004 | Messerly |
| 6,783,524 B2 | 8/2004 | Anderson et al. |
| 6,786,382 B1 | 9/2004 | Hoffman |
| 6,786,383 B2 | 9/2004 | Stegelmann |
| 6,790,216 B1 | 9/2004 | Ishikawa |
| 6,802,843 B2 | 10/2004 | Truckai et al. |
| 6,827,712 B2 | 12/2004 | Tovey et al. |
| 6,828,712 B2 | 12/2004 | Battaglin et al. |
| 6,869,439 B2 | 3/2005 | White et al. |
| 6,875,220 B2 | 4/2005 | Du et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,923,804 B2 | 8/2005 | Eggers et al. |
| 6,926,716 B2 | 8/2005 | Baker et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,677 B2 | 9/2005 | Nita et al. |
| 6,945,981 B2 | 9/2005 | Donofrio et al. |
| D511,145 S | 11/2005 | Donofrio et al. |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 7,001,335 B2 | 2/2006 | Adachi et al. |
| 7,011,657 B2 | 3/2006 | Truckai et al. |
| 7,033,357 B2 | 4/2006 | Baxter et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,378 B2 | 9/2006 | Salameh et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,124,932 B2 | 10/2006 | Isaacson et al. |
| 7,125,409 B2 | 10/2006 | Truckai et al. |
| 7,135,018 B2 | 11/2006 | Ryan et al. |
| 7,135,030 B2 | 11/2006 | Schwemberger et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,163,548 B2 | 1/2007 | Stulen et al. |
| 7,169,146 B2 | 1/2007 | Truckai et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,204,820 B2 | 4/2007 | Akahoshi |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,273,483 B2 | 9/2007 | Wiener et al. |
| 7,285,895 B2 | 10/2007 | Beaupré |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,331,410 B2 | 2/2008 | Yong et al. |
| 7,353,068 B2 | 4/2008 | Tanaka et al. |
| 7,354,440 B2 | 4/2008 | Truckal et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |

| | | | | | | |
|---|---|---|---|---|---|---|
| D576,725 S | 9/2008 | Shumer et al. | | 2003/0085632 A1* | 5/2003 | Take et al. .............. 310/323.19 |
| D578,643 S | 10/2008 | Shumer et al. | | 2003/0204199 A1 | 10/2003 | Novak et al. |
| D578,644 S | 10/2008 | Shumer et al. | | 2003/0212332 A1 | 11/2003 | Fenton et al. |
| D578,645 S | 10/2008 | Shumer et al. | | 2003/0212422 A1 | 11/2003 | Fenton et al. |
| 7,431,704 B2 | 10/2008 | Babaev | | 2003/0229344 A1 | 12/2003 | Dycus et al. |
| 7,441,684 B2 | 10/2008 | Shelton, IV et al. | | 2004/0030254 A1 | 2/2004 | Babaev |
| 7,455,208 B2 | 11/2008 | Wales et al. | | 2004/0047485 A1 | 3/2004 | Sherrit et al. |
| 7,472,815 B2 | 1/2009 | Shelton, IV et al. | | 2004/0054364 A1 | 3/2004 | Aranyi et al. |
| 7,473,263 B2 | 1/2009 | Johnston et al. | | 2004/0092921 A1 | 5/2004 | Kadziauskas et al. |
| 7,479,148 B2 | 1/2009 | Beaupre | | 2004/0097919 A1 | 5/2004 | Wellman et al. |
| 7,479,160 B2 | 1/2009 | Branch et al. | | 2004/0097996 A1 | 5/2004 | Rabiner et al. |
| 7,494,468 B2 | 2/2009 | Rabiner et al. | | 2004/0199193 A1 | 10/2004 | Hayashi et al. |
| 7,503,893 B2 | 3/2009 | Kucklick | | 2004/0204728 A1 | 10/2004 | Haefner |
| 7,503,895 B2 | 3/2009 | Rabiner et al. | | 2004/0243157 A1 | 12/2004 | Connor et al. |
| 7,506,790 B2 | 3/2009 | Shelton, IV | | 2004/0260300 A1 | 12/2004 | Gorensek et al. |
| 7,506,791 B2 | 3/2009 | Omaits et al. | | 2005/0021065 A1 | 1/2005 | Yamada et al. |
| 7,524,320 B2 | 4/2009 | Tierney et al. | | 2005/0033337 A1 | 2/2005 | Muir et al. |
| 7,534,243 B1 | 5/2009 | Chin et al. | | 2005/0049546 A1 | 3/2005 | Messerly et al. |
| D594,983 S | 6/2009 | Price et al. | | 2005/0070800 A1 | 3/2005 | Takahashi |
| 7,549,564 B2 | 6/2009 | Boudreaux | | 2005/0096683 A1 | 5/2005 | Ellins et al. |
| 7,559,450 B2 | 7/2009 | Wales et al. | | 2005/0143769 A1 | 6/2005 | White et al. |
| 7,567,012 B2 | 7/2009 | Namikawa | | 2005/0149108 A1 | 7/2005 | Cox |
| 7,578,820 B2 | 8/2009 | Moore et al. | | 2005/0165345 A1 | 7/2005 | Laufer et al. |
| 7,654,431 B2 | 2/2010 | Hueil et al. | | 2005/0177184 A1 | 8/2005 | Easley |
| 7,665,647 B2 | 2/2010 | Shelton, IV et al. | | 2005/0192610 A1 | 9/2005 | Houser et al. |
| 7,670,334 B2 | 3/2010 | Hueil et al. | | 2005/0209620 A1 | 9/2005 | Du et al. |
| 7,674,263 B2 | 3/2010 | Ryan | | 2005/0261581 A1 | 11/2005 | Hughes et al. |
| 7,691,098 B2 | 4/2010 | Wallace et al. | | 2005/0261588 A1 | 11/2005 | Makin et al. |
| 7,713,202 B2 | 5/2010 | Boukhny et al. | | 2005/0273090 A1 | 12/2005 | Nieman et al. |
| 7,714,481 B2 | 5/2010 | Sakai | | 2005/0288659 A1 | 12/2005 | Kimura et al. |
| D618,797 S | 6/2010 | Price et al. | | 2006/0030797 A1 | 2/2006 | Zhou et al. |
| 7,751,115 B2 | 7/2010 | Song | | 2006/0063130 A1 | 3/2006 | Hayman et al. |
| 7,770,774 B2 | 8/2010 | Mastri et al. | | 2006/0066181 A1* | 3/2006 | Bromfield et al. ............ 310/363 |
| 7,770,775 B2 | 8/2010 | Shelton, IV et al. | | 2006/0079878 A1 | 4/2006 | Houser |
| 7,780,054 B2 | 8/2010 | Wales | | 2006/0084963 A1 | 4/2006 | Messerly |
| 7,780,659 B2 | 8/2010 | Okada et al. | | 2006/0095046 A1 | 5/2006 | Trieu et al. |
| 7,784,662 B2 | 8/2010 | Wales et al. | | 2006/0190034 A1 | 8/2006 | Nishizawa et al. |
| 7,798,386 B2 | 9/2010 | Schall et al. | | 2006/0206115 A1 | 9/2006 | Schomer et al. |
| 7,806,891 B2 | 10/2010 | Nowlin et al. | | 2006/0211943 A1 | 9/2006 | Beaupre |
| 7,810,693 B2 | 10/2010 | Broehl et al. | | 2006/0235306 A1 | 10/2006 | Cotter et al. |
| 7,824,401 B2 | 11/2010 | Manzo et al. | | 2006/0253050 A1 | 11/2006 | Yoshimine et al. |
| 7,837,699 B2 | 11/2010 | Yamada et al. | | 2006/0264809 A1 | 11/2006 | Hansmann et al. |
| 7,854,735 B2 | 12/2010 | Houser et al. | | 2007/0016235 A1 | 1/2007 | Tanaka et al. |
| D631,155 S | 1/2011 | Peine et al. | | 2007/0016236 A1 | 1/2007 | Beaupre |
| 7,861,906 B2 | 1/2011 | Doll et al. | | 2007/0055228 A1 | 3/2007 | Berg et al. |
| 7,876,030 B2 | 1/2011 | Taki et al. | | 2007/0056596 A1 | 3/2007 | Fanney et al. |
| D631,965 S | 2/2011 | Price et al. | | 2007/0060915 A1 | 3/2007 | Kucklick |
| 7,892,606 B2 | 2/2011 | Thies et al. | | 2007/0060935 A1 | 3/2007 | Schwardt et al. |
| 7,905,881 B2 | 3/2011 | Masuda et al. | | 2007/0063618 A1 | 3/2007 | Bromfield |
| 7,922,651 B2 | 4/2011 | Yamada et al. | | 2007/0106317 A1 | 5/2007 | Shelton, IV et al. |
| 7,959,050 B2 | 6/2011 | Smith et al. | | 2007/0129716 A1 | 6/2007 | Daw et al. |
| 7,959,626 B2 | 6/2011 | Hong et al. | | 2007/0130771 A1 | 6/2007 | Ehlert et al. |
| 7,976,544 B2 | 7/2011 | McClurken et al. | | 2007/0131034 A1 | 6/2007 | Ehlert et al. |
| 7,998,157 B2 | 8/2011 | Culp et al. | | 2007/0149881 A1 | 6/2007 | Rabin |
| 8,038,693 B2 | 10/2011 | Allen | | 2007/0162050 A1 | 7/2007 | Sartor |
| 8,061,014 B2 | 11/2011 | Smith et al. | | 2007/0173872 A1 | 7/2007 | Neuenfeldt |
| 8,089,197 B2 | 1/2012 | Rinner et al. | | 2007/0185380 A1 | 8/2007 | Kucklick |
| 8,152,825 B2 | 4/2012 | Madan et al. | | 2007/0219481 A1 | 9/2007 | Babaev |
| 8,157,145 B2 | 4/2012 | Shelton, IV et al. | | 2007/0239028 A1 | 10/2007 | Houser et al. |
| 8,177,800 B2 | 5/2012 | Spitz et al. | | 2007/0249941 A1 | 10/2007 | Salehi et al. |
| D661,801 S | 6/2012 | Price et al. | | 2007/0260234 A1 | 11/2007 | McCullagh et al. |
| D661,802 S | 6/2012 | Price et al. | | 2007/0265560 A1 | 11/2007 | Soltani et al. |
| D661,803 S | 6/2012 | Price et al. | | 2007/0275348 A1 | 11/2007 | Lemon |
| D661,804 S | 6/2012 | Price et al. | | 2007/0282335 A1 | 12/2007 | Young et al. |
| 8,253,303 B2 | 8/2012 | Giordano et al. | | 2007/0287933 A1 | 12/2007 | Phan et al. |
| 2001/0025183 A1 | 9/2001 | Shahidi | | 2008/0009848 A1 | 1/2008 | Paraschiv et al. |
| 2001/0025184 A1 | 9/2001 | Messerly | | 2008/0051812 A1 | 2/2008 | Schmitz et al. |
| 2001/0031950 A1 | 10/2001 | Ryan | | 2008/0058585 A1 | 3/2008 | Novak et al. |
| 2001/0039419 A1 | 11/2001 | Francischelli et al. | | 2008/0058775 A1 | 3/2008 | Darian et al. |
| 2002/0002377 A1 | 1/2002 | Cimino | | 2008/0058845 A1 | 3/2008 | Shimizu et al. |
| 2002/0019649 A1 | 2/2002 | Sikora et al. | | 2008/0082039 A1 | 4/2008 | Babaev |
| 2002/0022836 A1 | 2/2002 | Goble et al. | | 2008/0082098 A1 | 4/2008 | Tanaka et al. |
| 2002/0049551 A1 | 4/2002 | Friedman et al. | | 2008/0171938 A1 | 7/2008 | Masuda et al. |
| 2002/0052617 A1 | 5/2002 | Anis et al. | | 2008/0172051 A1 | 7/2008 | Masuda et al. |
| 2002/0077550 A1 | 6/2002 | Rabiner et al. | | 2008/0177268 A1 | 7/2008 | Daum et al. |
| 2002/0156493 A1 | 10/2002 | Houser et al. | | 2008/0188878 A1 | 8/2008 | Young |
| 2003/0001456 A1* | 1/2003 | Kauf et al. .............. 310/323.18 | | 2008/0200940 A1 | 8/2008 | Eichmann et al. |
| 2003/0036705 A1 | 2/2003 | Hare et al. | | 2008/0208231 A1 | 8/2008 | Ota et al. |
| 2003/0055443 A1 | 3/2003 | Spotnitz | | 2008/0234708 A1 | 9/2008 | Houser et al. |

| | | |
|---|---|---|
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0243106 A1 | 10/2008 | Coe et al. |
| 2008/0245371 A1 | 10/2008 | Gruber |
| 2008/0249553 A1 | 10/2008 | Gruber et al. |
| 2008/0262490 A1 | 10/2008 | Williams |
| 2008/0281200 A1 | 11/2008 | Voic et al. |
| 2008/0287948 A1 | 11/2008 | Newton et al. |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036911 A1 | 2/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0105750 A1 | 4/2009 | Price et al. |
| 2009/0118802 A1 | 5/2009 | Mioduski et al. |
| 2009/0138006 A1 | 5/2009 | Bales et al. |
| 2009/0143795 A1 | 6/2009 | Robertson |
| 2009/0143796 A1 | 6/2009 | Stulen et al. |
| 2009/0143797 A1 * | 6/2009 | Smith et al. .................. 606/169 |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0143806 A1 | 6/2009 | Witt et al. |
| 2009/0149801 A1 | 6/2009 | Crandall et al. |
| 2009/0270853 A1 | 10/2009 | Yachi et al. |
| 2009/0270899 A1 | 10/2009 | Carusillo et al. |
| 2009/0318945 A1 | 12/2009 | Yoshimine et al. |
| 2009/0327715 A1 | 12/2009 | Smith et al. |
| 2010/0004668 A1 | 1/2010 | Smith et al. |
| 2010/0004669 A1 | 1/2010 | Smith et al. |
| 2010/0016785 A1 | 1/2010 | Takuma |
| 2010/0030248 A1 | 2/2010 | Palmer et al. |
| 2010/0036370 A1 | 2/2010 | Mirel et al. |
| 2010/0036405 A1 | 2/2010 | Giordano et al. |
| 2010/0069940 A1 | 3/2010 | Miller et al. |
| 2010/0158307 A1 * | 6/2010 | Kubota et al. ................. 381/400 |
| 2010/0179577 A1 | 7/2010 | Houser |
| 2010/0187283 A1 | 7/2010 | Crainich et al. |
| 2010/0193567 A1 | 8/2010 | Scheib et al. |
| 2010/0234906 A1 | 9/2010 | Koh |
| 2010/0268211 A1 | 10/2010 | Manwaring et al. |
| 2010/0298743 A1 | 11/2010 | Nield et al. |
| 2010/0298851 A1 | 11/2010 | Nield |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |
| 2011/0009850 A1 | 1/2011 | Main et al. |
| 2011/0015627 A1 | 1/2011 | DiNardo et al. |
| 2011/0015631 A1 | 1/2011 | Wiener et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0087256 A1 | 4/2011 | Wiener et al. |
| 2011/0125175 A1 | 5/2011 | Stulen et al. |
| 2011/0196286 A1 | 8/2011 | Robertson et al. |
| 2011/0196287 A1 | 8/2011 | Robertson et al. |
| 2011/0196398 A1 | 8/2011 | Robertson et al. |
| 2011/0196399 A1 | 8/2011 | Robertson et al. |
| 2011/0196400 A1 | 8/2011 | Robertson et al. |
| 2011/0196401 A1 | 8/2011 | Robertson et al. |
| 2011/0196402 A1 | 8/2011 | Robertson et al. |
| 2011/0196403 A1 | 8/2011 | Robertson et al. |
| 2011/0196404 A1 | 8/2011 | Dietz et al. |
| 2011/0196405 A1 | 8/2011 | Dietz |
| 2011/0288452 A1 | 11/2011 | Houser et al. |
| 2012/0029546 A1 | 2/2012 | Robertson |
| 2012/0059289 A1 | 3/2012 | Nield et al. |
| 2012/0078139 A1 | 3/2012 | Aldridge et al. |
| 2012/0078247 A1 | 3/2012 | Worrell et al. |
| 2012/0083783 A1 | 4/2012 | Davison et al. |
| 2012/0083784 A1 | 4/2012 | Davison et al. |
| 2012/0132450 A1 | 5/2012 | Timm et al. |
| 2012/0138660 A1 | 6/2012 | Shelton, IV |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0203257 A1 | 8/2012 | Stulen et al. |
| 2012/0205421 A1 | 8/2012 | Shelton, IV |
| 2012/0210223 A1 | 8/2012 | Eppolito |
| 2012/0211546 A1 | 8/2012 | Shelton, IV |
| 2012/0259353 A1 | 10/2012 | Houser et al. |
| 2012/0265196 A1 | 10/2012 | Turner et al. |
| 2012/0269676 A1 | 10/2012 | Houser et al. |
| 2012/0289984 A1 | 11/2012 | Houser et al. |
| 2012/0310262 A1 | 12/2012 | Messerly et al. |
| 2012/0310263 A1 | 12/2012 | Messerly et al. |
| 2012/0310264 A1 | 12/2012 | Messerly et al. |
| 2012/0323265 A1 | 12/2012 | Stulen |
| 2013/0012970 A1 | 1/2013 | Houser |

FOREIGN PATENT DOCUMENTS

| | | |
|---|---|---|
| CN | 1694649 A | 11/2005 |
| CN | 1922563 A | 2/2007 |
| CN | 101040799 A | 9/2007 |
| EP | 0171967 A2 | 2/1986 |
| EP | 0443256 A1 | 8/1991 |
| EP | 1832259 B1 | 11/1991 |
| EP | 1844720 A1 | 4/1992 |
| EP | 1862133 A1 | 12/1992 |
| EP | 0482195 B1 | 1/1996 |
| EP | 0612570 B1 | 6/1997 |
| EP | 1974771 A1 | 9/1998 |
| EP | 0908148 B1 | 1/2002 |
| EP | 0908155 B1 | 6/2003 |
| EP | 1199044 B1 | 12/2005 |
| EP | 1199043 B1 | 3/2006 |
| EP | 1433425 B1 | 6/2006 |
| EP | 1844720 A1 | 10/2007 |
| EP | 0612570 B1 | 12/2007 |
| EP | 1199045 B1 | 6/2008 |
| EP | 0908148 B1 | 10/2008 |
| EP | 1199044 B1 | 3/2009 |
| EP | 0443256 A1 | 6/2009 |
| EP | 2074959 A1 | 7/2009 |
| EP | 2298154 A2 | 3/2011 |
| GB | 2032221 A * | 4/1980 |
| GB | 2379878 B | 11/2004 |
| GB | 2447767 B | 8/2011 |
| JP | 62-2292153 A | 12/1987 |
| JP | 63-315049 A | 12/1988 |
| JP | 02-71510 U | 5/1990 |
| JP | 04-25707 U | 2/1992 |
| JP | 4-30508 U | 3/1992 |
| JP | 6-104503 A | 4/1994 |
| JP | 6-507081 A | 8/1994 |
| JP | 7-308323 A | 11/1995 |
| JP | 11-253451 A | 9/1999 |
| JP | 2002-186901 A | 7/2002 |
| JP | 2003-126110 A | 5/2003 |
| JP | 2003-310627 A | 5/2003 |
| JP | 2003-339730 A | 12/2003 |
| JP | 2005027026 A | 1/2005 |
| JP | 2005-534451 A | 11/2005 |

| | | | |
|---|---|---|---|
| JP | 2006217716 A | 8/2006 | |
| JP | 2008-508065 A | 3/2008 | |
| JP | 2008-119250 A | 5/2008 | |
| WO | WO 93/14708 A1 | 8/1993 | |
| WO | WO 94/21183 | 9/1994 | |
| WO | 7-508910 A | 10/1995 | |
| WO | WO 98/26739 A1 | 6/1998 | |
| WO | WO 01/54590 A1 | 8/2001 | |
| WO | WO 01/95810 A2 | 12/2001 | |
| WO | WO 2004/037095 A2 | 5/2004 | |
| WO | WO 2005/122917 A1 | 12/2005 | |
| WO | WO 2006/012797 A1 | 2/2006 | |
| WO | WO 2006/042210 A2 | 4/2006 | |
| WO | WO 2006/058223 A2 | 6/2006 | |
| WO | WO 2006/063199 A2 | 6/2006 | |
| WO | WO 2006/083988 A1 | 8/2006 | |
| WO | WO 2006/129465 A1 | 12/2006 | |
| WO | WO 2007/008710 A2 | 1/2007 | |
| WO | WO 2007/047531 A2 | 4/2007 | |
| WO | WO 01/54590 A1 | 12/2007 | |
| WO | WO 2008/016886 A2 | 2/2008 | |
| WO | WO 2008/042021 A1 | 4/2008 | |
| WO | WO 2008/130793 A1 | 10/2008 | |
| WO | WO 2009/018406 A2 | 2/2009 | |
| WO | 2009-511206 A | 3/2009 | |
| WO | WO 2011/144911 A1 | 11/2011 | |

OTHER PUBLICATIONS

Partial International Search Report for PCT/US2010/041663, Oct. 28, 2010 (2 pages).
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
U.S. Appl. No. 12/703,899, filed Feb. 11, 2010.
U.S. Appl. No. 29/361,917, filed May 17, 2010.
U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,411, filed Oct. 1, 2010.
U.S. Appl. No. 12/896,420, filed Oct. 1, 2010.
Technology Overview, printed from www.harmonicscalpel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
U.S. Appl. No. 29/327,737, filed Nov. 12, 2008.
U.S. Appl. No. 12/469,293, filed May 20, 2009.
U.S. Appl. No. 12/469,308, filed May 20, 2009.
U.S. Appl. No. 12/490,906, filed Jun. 24, 2009.
U.S. Appl. No. 12/490,922, filed Jun. 24, 2009.
U.S. Appl. No. 12/490,933, filed Jun. 24, 2009.
U.S. Appl. No. 12/490,948, filed Jun. 24, 2009.
U.S. Appl. No. 12/503,775, filed Jul. 15, 2009.
U.S. Appl. No. 12/503,769, filed Jul. 15, 2009.
U.S. Appl. No. 12/503,766, filed Jul. 15, 2009.
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
U.S. Appl. No. 13/195,352, filed Aug. 1, 2011.
U.S. Appl. No. 29/402,697, filed Sep. 26, 2011.
U.S. Appl. No. 29/402,699, filed Sep. 26, 2011.
U.S. Appl. No. 29/402,700, filed Sep. 26, 2011.
U.S. Appl. No. 29/402,701, filed Sep. 26, 2011.
U.S. Appl. No. 13/270,459, filed Oct. 11, 2011.
U.S. Appl. No. 13/251,766, filed Oct. 3, 2011.
International Preliminary Report on Patentability for PCT/US2010/041663, Jan. 17, 2012 (8 pages).
U.S. Appl. No. 29/404,676, filed Oct. 24, 2011.
U.S. Appl. No. 13/294,576, filed Nov. 11, 2011.
U.S. Appl. No. 13/448.175, filed Apr. 16, 2012.
U.S. Appl. No. 13/151,181, filed Jun. 2, 2011.
U.S. Appl. No. 13/369,561, filed Feb. 9, 2012.
U.S. Appl. No. 13/369,569, filed Feb. 9, 2012.
U.S. Appl. No. 13/369,578, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594. filed Feb. 9, 2012.
U.S. Appl. No. 13/369,601 filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
U.S. Appl. No. 13/545,292, filed Jul. 10, 2012.
U.S. Appl. No. 13/584,020, filed Aug. 13, 2012.
U.S. Appl. No. 13/584,445, filed Aug. 13, 2012.
U.S. Appl. No. 13/584,878, filed Aug. 14, 2012.
U.S. Appl. No. 13/585,124, filed Aug. 14, 2012.
U.S. Appl. No. 13/585,292, filed Aug. 14, 2012.

* cited by examiner

ROTATING TRANSDUCER MOUNT FOR ULTRASONIC SURGICAL INSTRUMENTS

BACKGROUND

The present disclosure generally relates to ultrasonic surgical systems and, more particularly, to ultrasonic systems that allow surgeons to perform cutting and coagulation.

Ultrasonic surgical instruments are finding increasingly widespread applications in surgical procedures by virtue of the unique performance characteristics of such instruments. Depending upon specific instrument configurations and operational parameters, ultrasonic surgical instruments can provide substantially simultaneous cutting of tissue and homeostasis by coagulation, desirably minimizing patient trauma. The cutting action is typically realized by an-end effector, or blade tip, at the distal end of the instrument, which transmits ultrasonic energy to tissue brought into contact with the end effector. Ultrasonic instruments of this nature can be configured for open surgical use, laparoscopic, or endoscopic surgical procedures including robotic-assisted procedures.

Some surgical instruments utilize ultrasonic energy for both precise cutting and controlled coagulation. Ultrasonic energy cuts and coagulates by using lower temperatures than those used by electrosurgery. Vibrating at high frequencies (e.g., 55,500 times per second), the ultrasonic blade denatures protein in the tissue to form a sticky coagulum. Pressure exerted on tissue with the blade surface collapses blood vessels and allows the coagulum to form a hemostatic seal. The precision of cutting and coagulation is controlled by the surgeon's technique and adjusting the power level, blade edge, tissue traction, and blade pressure.

A primary challenge of ultrasonic technology for medical devices, however, continues to be sealing of blood vessels. Work done by the applicant and others has shown that optimum vessel sealing occurs when the inner muscle layer of a vessel is separated and moved away from the adventitia layer prior to the application of standard ultrasonic energy. Current efforts to achieve this separation have involved increasing the clamp force applied to the vessel.

Furthermore, the user does not always have visual feedback of the tissue being cut. Accordingly, it would be desirable to provide some form of feedback to indicate to the user that the cut is complete when visual feedback is unavailable. Moreover, without some form of feedback indicator to indicate that the cut is complete, the user may continue to activate the harmonic instrument even though the cut is complete, which cause possible damage to the harmonic instrument and surrounding tissue by the heat that is generated exponentially when activating a harmonic instrument with nothing between the jaws.

It would be desirable to provide an ultrasonic surgical instrument that overcomes some of the deficiencies of current instruments. The ultrasonic surgical instrument described herein overcomes those deficiencies.

SUMMARY

In one general aspect, various embodiments are directed to an ultrasonic surgical instrument that comprises a transducer configured to produce vibrations along a longitudinal axis at a predetermined frequency. In various embodiments, an ultrasonic blade extends along the longitudinal axis and is coupled to the transducer. In various embodiments, the ultrasonic blade includes a body having a proximal end and a distal end, wherein the distal end is movable relative to the longitudinal axis by the vibrations produced by the transducer.

In one general aspect, various embodiments are directed to an ultrasonic surgical instrument that comprises a handpiece housing that operably supports an electrical contact assembly therein that is in electrical communication with a signal source. An acoustic assembly is supported within the handpiece housing in rotatable contact with the electrical contact assembly. In various embodiments, the signal source produces at least one of an ultrasonic signal and a radio frequency signal.

FIGURES

The features of various embodiments are set forth with particularity in the appended claims. The various embodiments, however, both as to organization and methods of operation, together with further objects and advantages thereof, may best be understood by reference to the following description, taken in conjunction with the accompanying drawings as follows.

DESCRIPTION

Figure 1:
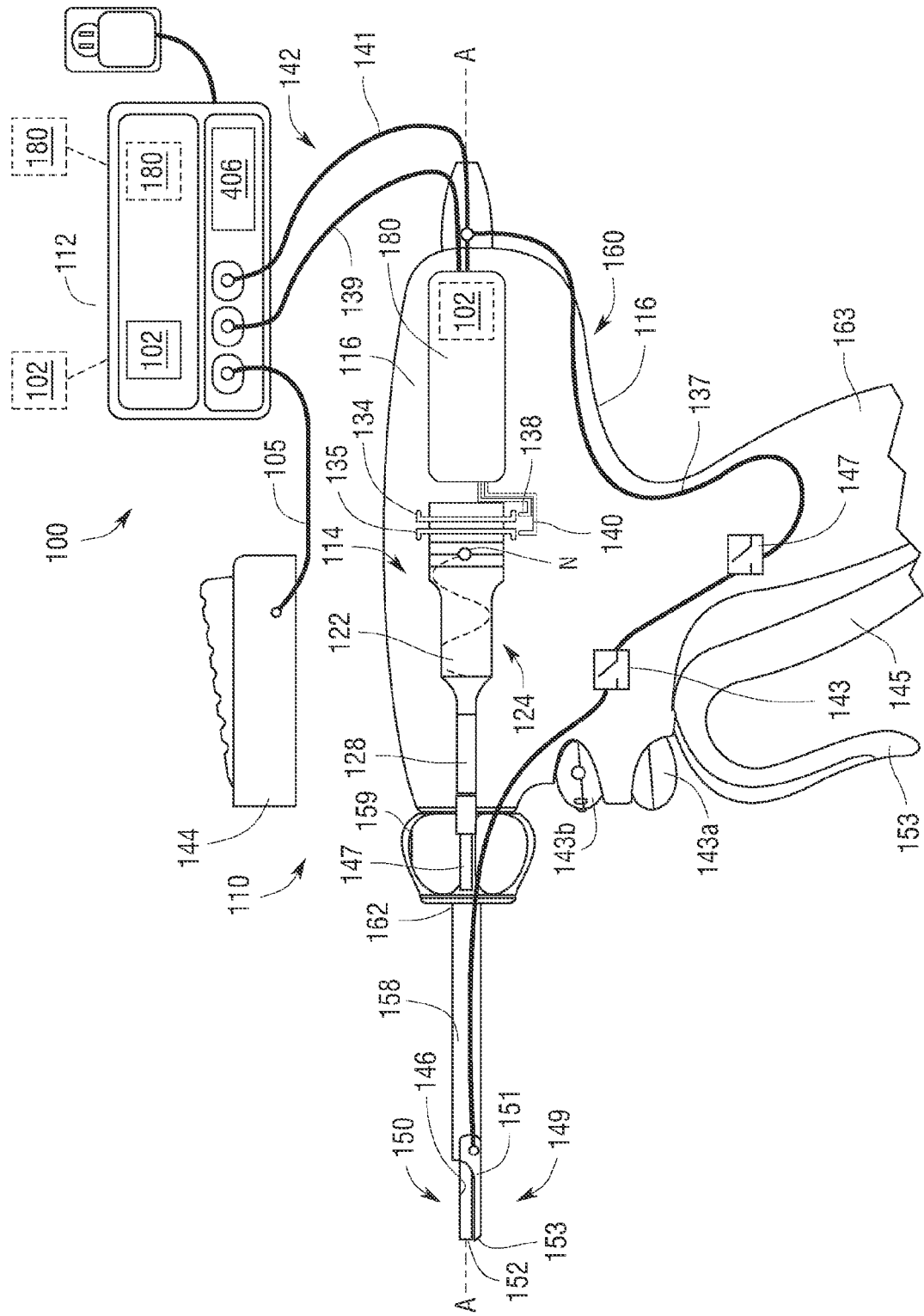
FIG. 1 illustrates a surgical instrument comprising an ultrasonic surgical instrument system and an electrosurgery surgical instrument system.

Before explaining various embodiments of ultrasonic surgical instruments in detail, it should be noted that the illustrative embodiments are not limited in application or use to the details of construction and arrangement of parts illustrated in the accompanying drawings and description. The illustrative embodiments may be implemented or incorporated in other embodiments, variations and modifications, and may be practiced or carried out in various ways. Further, unless otherwise indicated, the terms and expressions employed herein have been chosen for the purpose of describing the illustrative embodiments for the convenience of the reader and are not for the purpose of limitation thereof.

Further, it is understood that any one or more of the following-described embodiments, expressions of embodiments, examples, can be combined with any one or more of the other following-described embodiments, expressions of embodiments, and examples.

Various embodiments are directed to improved ultrasonic surgical instruments configured for effecting tissue dissecting, cutting, and/or coagulation during surgical procedures. In one embodiment, an ultrasonic surgical instrument apparatus is configured for use in open surgical procedures, but has applications in other types of surgery, such as laparoscopic, endoscopic, and robotic-assisted procedures. Versatile use is facilitated by selective use of ultrasonic energy.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

The various embodiments will be described in combination with an ultrasonic instrument as described herein. Such description is provided by way of example, and not limitation, and is not intended to limit the scope and applications thereof. For example, any one of the described embodiments is useful in combination with a multitude of ultrasonic instruments including those described in, for example, U.S. Pat. Nos. 5,322,055; 5,449,370; 5,630,420; 5,935,144; 5,938,633; 5,944,737; 5,954,736; 6,278,218; 6,283,981; 6,309,400; 6,325,811; and 6,436,115, wherein the disclosure of each of the patents is herein incorporated by reference. Also incorporated by reference in its entirety is commonly-owned, U.S. patent application Ser. No. 11/726,625, entitled ULTRASONIC SURGICAL INSTRUMENTS, filed on Mar. 22, 2007, now U.S. Pat. App. Pub. No. 2008/0234710. The disclosure of each of the following commonly-owned, contemporaneously-filed U.S. patent applications is incorporated herein by reference in its entirety:

(1) U.S. patent application Ser. No. 12/503,769, entitled "ULTRASONIC SURGICAL INSTRUMENTS," now U.S. Pat. App. Pub. No. 2011/0015631; and (2) U.S. patent application Ser. No. 12/503,766, entitled "ULTRASONIC SURGICAL INSTRUMENTS," now U.S. Pat. App. Pub. No. 2011/0015627.

(3) U.S. patent application Ser. No. 12/503,775, entitled "ULTRASONIC DEVICE FOR CUTTING AND COAGULATING WITH STEPPED OUTPUT," now U.S. Pat. No. 8,058,771.

As will become apparent from the following description, it is contemplated that embodiments of the surgical instrument described herein may be used in association with an oscillator module of a surgical system, whereby ultrasonic energy from the oscillator module provides the desired ultrasonic actuation for the present surgical instrument. It is also contemplated that embodiments of the surgical instrument described herein may be used in association with a signal generator module of a surgical system, whereby electrical energy in the form of radio frequencies (RF), for example, is used to provide feedback to the user regarding the surgical instrument. The ultrasonic oscillator and/or the signal generator modules may be non-detachably integrated with the surgical instrument or may be provided as separate components, which can be electrically attachable to the surgical instrument.

One embodiment of the present surgical apparatus is particularly configured for disposable use by virtue of its straightforward construction. However, it is also contemplated that other embodiments of the present surgical instrument can be configured for non-disposable or multiple uses. Detachable connection of the present surgical instrument with an associated oscillator and signal generator unit is presently disclosed for single-patient use for illustrative purposes only. However, non-detachable integrated connection of the present surgical instrument with an associated oscillator and/or signal generator unit is also contemplated. Accordingly, various embodiments of the presently described surgical instruments may be configured for single use and/or multiple uses and with either detachable and/or non-detachable integral oscillator and/or signal generator modules, without limitation. All combinations of such configurations are contemplated to be within the scope of the present disclosure.

FIG. 1 illustrates one embodiment of a surgical system 100. The surgical system 100 includes a generator 112 and an ultrasonic surgical instrument 110. The generator 112 is connected to an ultrasonic transducer 114 portion of the ultrasonic surgical instrument 110 via a suitable transmission medium such as a cable 142. In one embodiment, the generator 112 is coupled to an ultrasonic generator module 180 and a signal generator module 102. In various embodiments, the ultrasonic generator module 180 and/or the signal generator module 102 each may be formed integrally with the generator 112 or may be provided as a separate circuit modules electrically coupled to the generator 112 (shown in phantom to illustrate this option). In one embodiment, the signal generator module 102 may be formed integrally with the ultrasonic generator module 180. Although in the presently disclosed embodiment, the generator 112 is shown separate from the surgical instrument 110, in one embodiment, the generator 112 may be formed integrally with the surgical instrument 110 to form a unitary surgical system 100. The generator 112 comprises an input device 406 located on a front panel of the generator 112 console. The input device 406 may comprise any suitable device that generates signals suitable for programming the operation of the generator 112 as subsequently described with reference to FIG. 18. Still with reference to FIG. 1, the cable 142 may comprise multiple electrical conductors 139, 141 for the application of electrical energy to positive (+) and negative (−) electrodes of the ultrasonic transducer 114. It will be noted that, in some applications, the ultrasonic transducer 114 may be referred to as a "handle assembly" because the surgical instrument 110 of the surgical system 100 may be configured such that a surgeon may grasp and manipulate the ultrasonic transducer 114 during various procedures and operations.

In one embodiment, the generator 112 may be implemented as an electrosurgery unit (ESU) capable of supplying power sufficient to perform bipolar electrosurgery using radio frequency (RF) energy. In one embodiment, the ESU can be a bipolar ERBE ICC 350 sold by ERBE USA, Inc. of Marietta, Ga. In bipolar electrosurgery applications, as previously discussed, a surgical instrument having an active electrode and a return electrode can be utilized, wherein the active electrode and the return electrode can be positioned against, or adjacent to, the tissue to be treated such that current can flow from the active electrode to the return electrode through the tissue. Accordingly, the generator 112 may be configured for therapeutic purposes by applying electrical energy to the tissue T sufficient for treating the tissue (e.g., cauterization).

In one embodiment, the signal generator module 102 may be configured to deliver a subtherapeutic RF signal to implement a tissue impedance measurement module. In one embodiment, the signal generator module 102 comprises a bipolar radio frequency generator as described in more detail below. In one embodiment, signal generator module 102 may be configured to monitor the electrical impedance $Z_t$ of tissue T (FIG. 5) and to control the characteristics of time and power level based on the tissue impedance $Z_t$. The tissue impedance $Z_t$ may be determined by applying the subtherapeutic RF signal to the tissue T and measuring the current through the tissue T (FIGS. 5, 10, 16, 17) by way of a return electrode on provided on a clamp member 151, as discussed in more detail below. Accordingly, the signal generator module 102 may be configured for subtherapeutic purposes for measuring the impedance or other electrical characteristics of the tissue T. Techniques and circuit configurations for measuring the impedance or other electrical characteristics of the tissue T are discussed in more detail below with reference to FIGS. 18-20 below.

A suitable ultrasonic generator module 180 may be configured to functionally operate in a manner similar to the GEN 300 sold by Ethicon Endo-Surgery, Inc. of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting a Loose Blade in a Handle Connected to an Ultrasonic Surgical System); U.S. Pat. No. 6,626,926 (Method for Driving an Ultrasonic System to Improve Acquisition of Blade Resonance Frequency at Startup); U.S. Pat. No. 6,633,234 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,621 (Output Displacement Control Using Phase Margin in an Ultrasonic Surgical Handle); U.S. Pat. No. 6,679,899 (Method for Detecting Transverse Vibrations in an Ultrasonic Handle); U.S. Pat. No. 6,908,472 (Apparatus and Method for Altering Generator Functions in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

In accordance with the described embodiments, the ultrasonic generator module 180 produces electrical signals of a particular voltage, current, and frequency, e.g. 55,500 cycles per second (Hz). The generator is 112 connected by the cable 142 to the ultrasonic generator module 180 in the handpiece assembly 160, which contains piezoceramic elements forming the ultrasonic transducer 114. In response to a switch 143 on the handpiece assembly 160 or a foot switch 144 connected to the generator 112 by another cable 105 the generator signal is applied to the transducer 114, which causes a longitudinal vibration of its elements. A structure connects the transducer 114 to a surgical blade 146, which is thus vibrated at ultrasonic frequencies when the generator signal is applied to the transducer 114. The structure is designed to resonate at the selected frequency, thus amplifying the motion initiated by the transducer 114. In one embodiment, the generator 112 is configured to produce a particular voltage, current, and/or frequency output signal that can be stepped with high resolution, accuracy, and repeatability.

Figure 2:
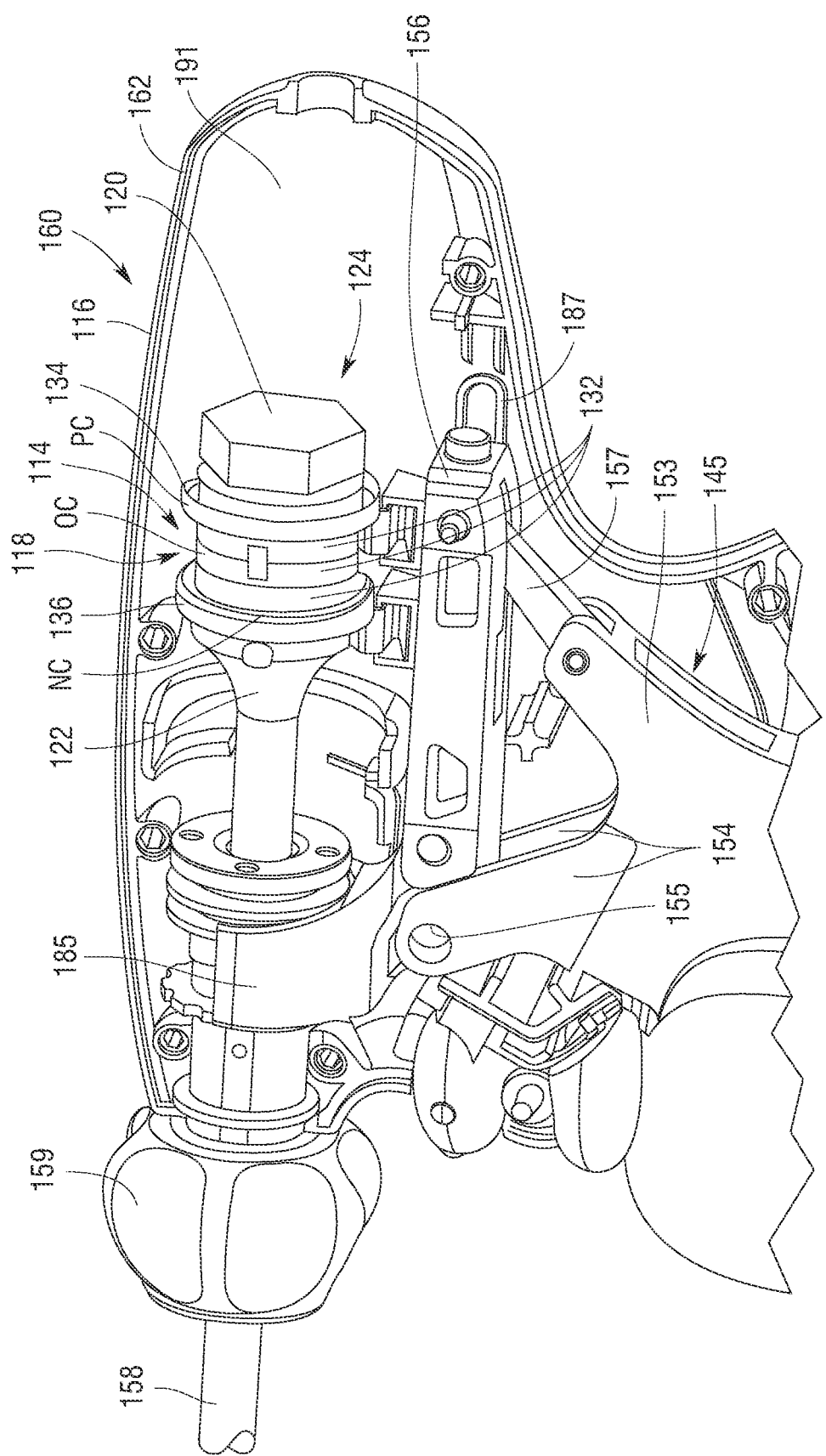
FIG. 2 illustrates a portion of a handpiece assembly of the surgical instrument of FIG. 1 with a portion of the handpiece housing removed and an acoustic assembly operably engaged with a waveguide of the surgical instrument.
Figure 3:
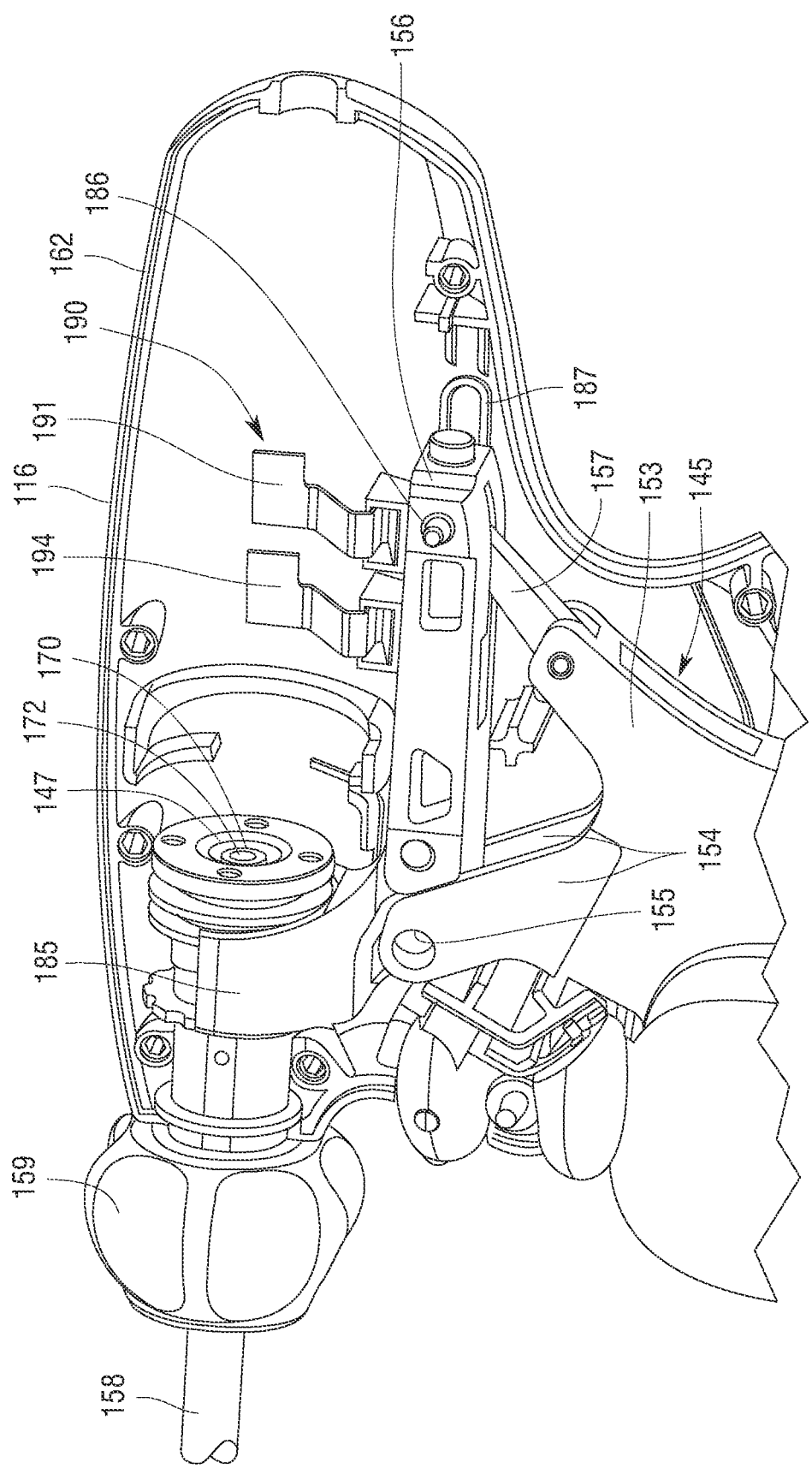
FIG. 3 illustrates the handpiece assembly of FIG. 2 with the acoustic assembly removed to illustrate positive and negative electrode contacts configured to supply the acoustic assembly with power.

Referring now to FIGS. 1-4, the handpiece assembly 160 of the surgical instrument system 110 may include a handpiece housing 116 that operably supports the end effector 150. The handpiece housing 116 rotatably supports an acoustic assembly 124 therein. The acoustic assembly 124 includes the ultrasonic transducer 114 that generally includes a transduction portion 118, a first resonator or end-bell 120, a second resonator or fore-bell 122, and ancillary components as shown in FIG. 2. In various embodiments, the ultrasonic energy produced by the transducer 114 can be transmitted through the acoustic assembly 124 to the end effector 150 via the ultrasonic transmission waveguide 147 as shown in FIGS. 1 and 3. In order for the acoustic assembly 124 to deliver energy to the waveguide 147, and ultimately to the end effector 150, the components of the acoustic assembly 124 are acoustically coupled to the blade 146. For example, the distal end of the ultrasonic transducer 114 may be acoustically coupled to the proximal end 170 of the waveguide 146 by a coupling assembly that enables the acoustic assembly 124 to freely rotate relative to the waveguide 147 while transmitting ultrasonic energy thereto.

Figure 4:
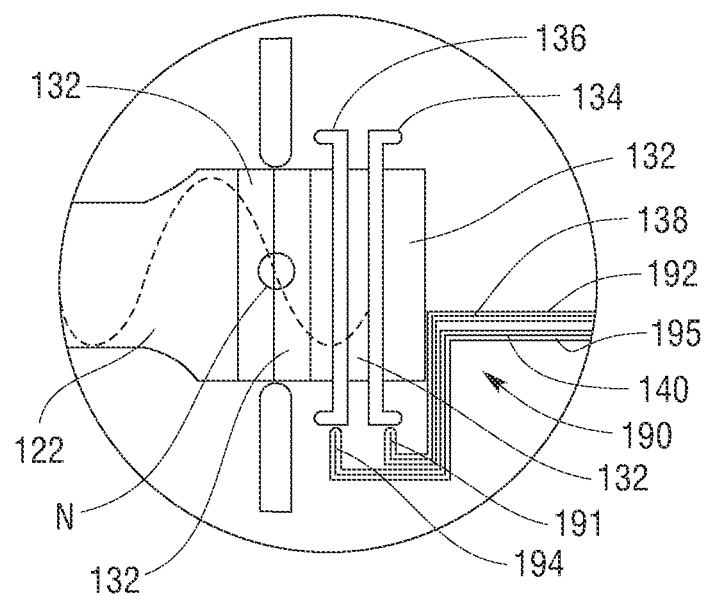
FIG. 4 is a detail view of a portion of the acoustic assembly of FIG. 2.

As shown in FIG. 3, the proximal end 170 of the waveguide 146 may be provided with an aperture 172 therein that is sized to receive a stem (not shown) that protrudes distally from the fore-bell 122. In various embodiments, piezoelectric elements 132, for example, can be compressed between the end-bell 120 and the fore-bell 122 to form a stack of piezoelectric elements when the end-bell 120 and the fore-bell 122 are assembled together as illustrated in FIGS. 2-4. The piezoelectric elements 132 may be fabricated from any suitable material, such as, for example, lead zirconate-titanate, lead meta-niobate, lead titanate, and/or any suitable piezoelectric crystal material, for example. As shown in FIGS. 2 and 4, the transducer 114 may comprise electrodes, such as at least one positive electrode 134 and at least one negative electrode 136, for example, which can be configured to create a voltage potential across the one or more piezoelectric elements 132. As shown in FIG. 2, the positive electrode 134 and the negative electrode 136, and the piezoelectric elements 132 can each be configured with a bore (not shown) that cooperates to form a passageway that can receive a threaded portion of the end-bell 120. In one embodiment, the positive electrode 134 is provided in the form of an annular ring that has a first circumference "PC" and the negative electrode 136 is also provided in the form of an annular ring that has a second circumference "NC." As shown in FIG. 2, in various embodiments, the stack of piezoelectric elements 132 may have an outer circumference "OC" that is less than the first and second circumferences "PC" and "NC."

In various embodiments, the handpiece housing 116 may support the ultrasonic generator module 180 and/or the signal generator module 102. In one embodiment, the ultrasonic generator module 180 may be electrically coupled to an electrical contact assembly 190 that may comprise a positive slip ring contact 191 that is mounted within handpiece housing 116 for rotatable contact with the positive electrode 134. The positive slip ring contact 191 is electrically coupled to the ultrasonic generator module 180 by a positive ultrasonic supply cable/conductor 192. The electrical contact assembly 190 may further comprise a negative slip ring contact 194 that is mounted within handpiece housing 116 for rotatable contact with the negative electrode 136. The negative slip ring contact 194 is electrically coupled to the ultrasonic generator module 180 by a negative ultrasonic supply cable 195. It will be appreciated that such arrangement enables the acoustic assembly 124 to freely rotate relative to the ultrasonic generator module 180 while remaining in full electrical contact therewith.

In various embodiments, the ultrasonic transmission waveguide 147 may comprise a plurality of stabilizing silicone rings or compliant supports (not shown) positioned at, or at least near, a plurality of nodes. As was discussed above, the silicone rings can dampen undesirable vibration and isolate the ultrasonic energy from the sheath 158 that at least partially surrounds the waveguide 147, thereby assuring the flow of ultrasonic energy in a longitudinal direction to the distal end 152 of the end effector 150 with maximum efficiency.

As shown in FIGS. 2 and 3, the sheath 158 can be coupled to a rotation wheel 159 that is rotatably attached to the distal end of the handpiece assembly 160. The rotation wheel 159 facilitates selective rotation of the sheath 158 and the waveguide 147 relative to the handpiece assembly 160. The sheath 158 may have an adapter portion 162 that may be threaded or snapped onto the rotation wheel 159. The rotation wheel 159 may include a flanged portion (not shown) that is snapped into an annular groove in the handpiece assembly 160 to facilitate rotation of the sheath 158 and waveguide 146 relative to the handpiece assembly 160 about axis A-A. In one embodiment, the sheath 158 also includes a hollow tubular portion 164 through which the waveguide 146 extends in the manner described in further detail above. In various embodiments, the adapter 162 of the sheath 158 may be constructed from ULTEM®, for example, and the tubular portion 164 may be fabricated from stainless steel, for example. In at least one embodiment, the ultrasonic transmission waveguide 147 may have polymeric material, for example, surrounding it in order to isolate it from outside contact.

In the embodiment, as shown in FIG. 1, the ultrasonic generator module 180 is electrically coupled to the electronic signal/radio frequency generator 112 by the cables 139, 141 which may be housed in a sheath to form the cable 142. Because the acoustic assembly 124 can freely rotate relative to the ultrasonic generator module 180, the waveguide 147 and the end effector 150 may be freely rotated about axis A-A relative to the handpiece assembly 160 without causing the cable 142 to undesirably twist and tangle.

As illustrated in FIGS. 2 and 3, the handpiece assembly 160 may have a pistol grip configuration and operably support a movable trigger assembly 145 that is pivotally supported within the handpiece assembly 160. To facilitate easy assembly, the handpiece assembly 160 may comprise two housing segments 162 that are coupled together by threaded fasteners, snap features, adhesive. The movable trigger assembly 145 includes a trigger portion 153 that has a pair of spaced attachment arms 154 that each has a hole 155 therethrough. Holes 155 are each sized to receive a corresponding pivot pin (not shown) that protrudes from each of the housing segments 162. Such arrangement permits the trigger portion 153 to pivot relative to the handpiece assembly 160 about an axis that is substantially transverse to axis A-A.

As shown in FIGS. 2 and 3, the trigger assembly 145 may comprise an actuation arm 156 that is attached to the trigger portion 153 via an intermediate link 157. The actuation arm 156 is pivotally coupled (pinned) to the trigger yoke 185. The arm 156 has a mounting pin 186 extending transversely therethrough that is sized to be slidably received in corresponding elongated cavities 187 formed in the housing segments 162. See FIGS. 2 and 3. Such arrangement facilitates the axial movement of the actuation arm 156 within the handpiece assembly 160 in response to pivoting the trigger portion 153.

In the embodiment illustrated in FIG. 1, the end effector 150 portion of the surgical system 100 comprises a clamp arm assembly 149 connected at a distal end of the surgical instrument 110. The blade 146 forms a first (e.g., energizing) electrode and the clamp arm assembly 149 comprises an electrically conductive portion that forms a second (e.g., return) electrode. The signal generator module 102 is coupled to the blade 146 and the clamp arm assembly 149 through a suitable transmission medium such as a cable 137. The cable 137 comprises multiple electrical conductors for applying a voltage to the tissue and providing a return path for current flowing through the tissue back to the signal generator module 102. In various embodiments, the signal generator module 102 may be formed integrally with the generator 112 or may be provided as a separate circuit coupled to the generator 112 and, in one embodiment, may be formed integrally with the ultrasonic generator module 180 (shown in phantom to illustrate these options).

In one embodiment, the surgical system 100 illustrated in FIG. 1 may comprise components for selectively energizing an end effector 150 and transmitting mechanical energy thereto and, in addition, selectively energizing the end effector 150 with therapeutic and/or subtherapeutic electrical energy. The surgical instrument 110 may be switchable between a first operating mode in which mechanical energy, or vibrations at ultrasonic frequencies (e.g., 55.5 kHz), are transmitted to the end effector 150 and a second operating mode in which electrical energy (e.g., therapeutic and/or subtherapeutic), or current, is permitted to flow through the end effector 150. In certain embodiments, referring to FIG. 1, in a first operating mode of the surgical instrument 110, for example, the transducer 114 converts electrical energy supplied thereto by the ultrasonic generator module 180 (e.g., an ultrasonic oscillator) of the generator 112 into mechanical vibrations and transmit the vibrations into a waveguide 147 to the blade 146 portion of the end effector 150, for example. Such mechanical vibrations can be generated at ultrasonic frequencies, although any suitable frequency, or frequencies, can be used. In the second operating mode of the surgical instrument 110, an electrical current may be supplied by the generator 112 that can flow through the transducer 114, the waveguide 147, and the end effector 150. The current flowing through the waveguide 147 and end effector 150 can be an alternating current (AC current), wherein, in various embodiments, the wave form of the AC current can be sinusoidal and/or may comprise a series of step intervals, for example.

In one embodiment, the current supplied by the signal generator module 102 is an RF current. In any event, the surgical instrument 110 may comprise a supply path and a return path, wherein the tissue T (FIG. 5) being treated completes, or closes, an electrical circuit, or loop, comprising a supply path through the transducer 114, the waveguide 147, and the blade 146 and a return path through conductor cable 137. In one embodiment, the patient can be positioned on a conductive pad wherein the current can flow from a supply path of the surgical instrument, through the patient, and into the conductive pad in order to complete the electrical circuit.

Still referring to FIG. 1, as previously discussed, in one embodiment the surgical instrument system 110 may be energized by the generator 112 by way of the foot switch 144 in order to energize the end effector 150. When actuated, the foot switch 144 triggers the generator 112 to deliver electrical energy to the handpiece assembly 160, for example. Although the foot switch 144 may be suitable in many circumstances, other suitable switches can be used. In various embodiments, the surgical instrument system 110 may comprise at least one supply conductor 139 and at least one return conductor 141, wherein current can be supplied to handpiece assembly 160 via the supply conductor 139 and wherein the current can flow back to the generator 112 via return conductor 141. In various embodiments, the supply conductor 139 and the return conductor 141 may comprise insulated wires and/or any other suitable type of conductor. In certain embodiments, as described below, the supply conductor 139 and the return conductor 141 may be contained within and/or may comprise a cable extending between, or at least partially between, the generator 112 and the transducer 114 portion of the handpiece assembly 160. In any event, the generator 112 can be configured to apply a sufficient voltage differential between the supply conductor 139 and the return conductor 141 such that sufficient current can be supplied to the transducer 114.

In various embodiments, still referring to FIG. 1, the supply conductor 139 and the return conductor 141 may be operably connected to a transducer drive unit 135, wherein the drive unit 135 can be configured to receive current from the generator 112 via the supply conductor 139. In certain embodiments, the handpiece assembly 160 may comprise a switch, such as a toggle switch 143, for example, which can be manipulated to place the surgical instrument 110 in one of a first operating mode and a second operating mode. In one embodiment, as described below, the toggle switch 143 may comprise a first toggle button 143*a* which can be depressed to place the surgical instrument 110 in the first operating mode and, in addition, a second toggle button 143*b* which can be depressed to place the surgical instrument in the second operating mode. Although a toggle switch is illustrated and described herein, any suitable switch, or switches, can be used. When the first toggle button 143*a* is depressed, the transducer drive unit 135 can operate a transducer, such as the transducer 114, for example, such that the transducer 114 produces vibrations. The transducer 114 may comprise one or more piezoelectric elements 132, wherein the drive unit 135 can be configured to apply a voltage differential, and/or a series of voltage differentials, across the piezoelectric elements 132 such that they mechanically vibrate in a desired manner. Also, the transducer 114 may comprise one or more electrodes, such as a positive electrode 134 and a negative electrode 136, for example, positioned intermediate and/or adjacent to the piezoelectric elements 132. In one embodiment, the surgical instrument 110 may comprise a positive polarizing conductor 192 operably connected to the drive unit 135 and a positive electrode 134 and, in addition, a negative polarizing conductor 195 operably connected to the drive unit 135 and the negative electrode 136, wherein the drive unit 135 can be configured to polarize the electrodes 134, 136 via the polarizing conductors 192, 195, respectively.

In various embodiments, the transducer 114 may comprise a fore-bell 122 and a velocity transformer 128 which can be configured to conduct the vibrations produced by the piezoelectric elements 132 into the transmission waveguide 147. In certain embodiments, referring still to FIG. 1, the transmission waveguide 147 may comprise an elongate shaft portion surrounded, or at least partially surrounded, by a sheath 158, for example, wherein the waveguide 147 may comprise a distal end 152. The distal end 152 of the waveguide 147 may comprise part of the end effector 150, wherein the end effector 150 may comprise the clamp member 151 having a rotatable clamp arm, or jaw, which can be pivoted between an open position in which tissue can be positioned intermediate the blade 146 and the clamp member 151 and a closed position in which clamp member 151 can position and/or compress the tissue T (FIG. 5) against the blade 146. In various embodiments, a surgical instrument may comprise a lever or actuator, such as a jaw closure trigger 145, for example, which can be actuated by a surgeon in order to pivot the clamp member 151 between its open and closed positions. In at least one embodiment, the jaw closure trigger 145 can be operably engaged with a push/pull rod operably engaged with the clamp member 151 wherein, when the jaw closure trigger 145 is closed or moved toward the handpiece assembly 160, the closure trigger 145 can push the push/pull rod distally and pivot the clamp member 151 toward the blade 146 into its closed position. Correspondingly, the jaw closure trigger 145 can be pivoted into its open position in order to pull the rod proximally and pivot the clamp member 151 away from the blade 146 into its open position.

In any event, once the tissue T (FIG. 5) has been suitably positioned within the jaws of the end effector 150, the transducer 114 can be operated by the drive unit 135 in order to transmit mechanical energy, or vibrations, into the targeted tissue T. In some embodiments, the actuation of the foot switch 144 may be sufficient to actuate the transducer 114. In certain other embodiments, the actuation of a different switch may be required in addition to or in lieu of the actuation of the foot switch 144. In one embodiment, the actuation of the foot switch 144 can supply power to the drive unit 135, although the actuation of the jaw closure trigger 145, and the trigger closure switch 147, may be required before the drive unit 135 can drive the transducer 114. In various embodiments, the jaw closure trigger 145 can be moved between a first, or open, position in which the trigger closure switch 147 is in an open state, or condition, and a second, or closed, position in which the trigger closure switch 147 is in a closed state, or condition. When the trigger closure switch 147 is in its closed condition, in various embodiments, a circuit within the drive unit 135, for example, can be closed such that the drive unit 135 can drive the transducer 114.

Figure 5:
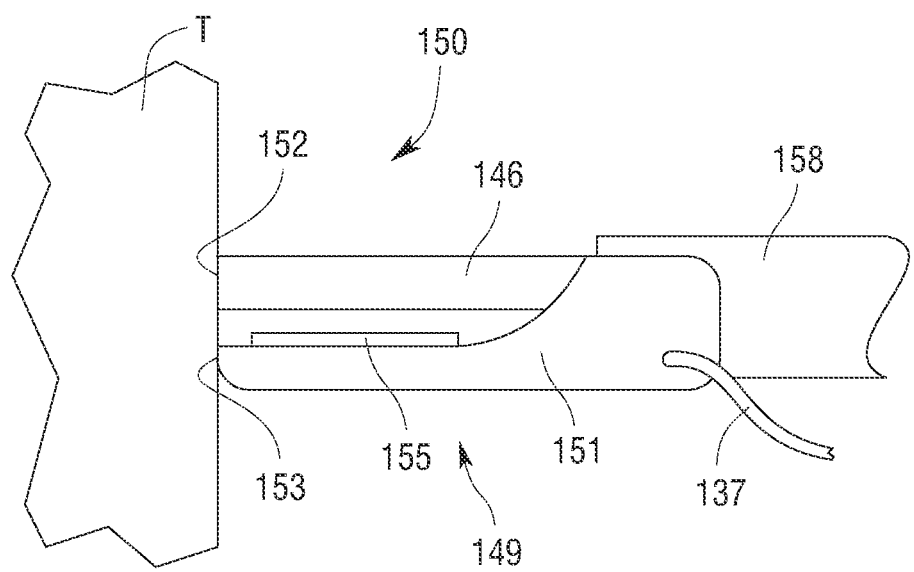
FIG. 5 is a detail view of the end effector of the ultrasonic surgical instrument of FIG. 1.

Referring still to FIG. 1, In various applications, a surgeon may desire to treat tissue using mechanical energy, or vibrations, transmitted through the blade 146, for example. In various other applications, the surgeon may desire to treat the tissue using therapeutic electrical energy transmitted through the blade 146. In various other applications, the surgeon may desire to obtain feedback in regards to a state of the tissue T (FIG. 5) by measuring the electrical properties of the tissue T (e.g., impedance) using subtherapeutic electrical energy transmitted through the blade 146. In various embodiments, the toggle switch 143 can be manipulated to place the surgical instrument 110 in the second operating mode. In at least one such embodiment, the second toggle button 143b of the toggle switch 143 can be depressed in order to switch the surgical instrument 110 from the first operating mode into the second operating mode. As described below, the depression of the second toggle button 143b can configure the handpiece assembly 160 such that the drive unit 135 does not drive the transducer 114 but rather, the power supplied to the handpiece assembly 160 from generator 112 can flow into the blade 146 without being converted into mechanical energy, or vibrations. In one embodiment, referring now to FIG. 5, the distal end 152 of the blade 146 can be positioned against the targeted tissue "T" and, in addition, the distal end 153 of the clamp member 151 can also be positioned against the tissue T such that current can flow from the supply conductor 139 into the blade 136, through the tissue T, and return back to the generator 112 via the clamp member 151, the return conductors 137, 141. As shown in FIG. 5, the clamp member 151 can be configured such that it is not in contact with the blade 146 when the clamp member 151 is in the closed position.

With reference now back to FIG. 1, in various embodiments, the return conductor 137 may comprise an insulated wire having a first end operably coupled with the clamp member 151 and a second end operably coupled with the return conductor 141, wherein current can flow through the return conductor 137 when the toggle switch 143 is in the second configuration and the trigger closure switch 147 has been closed by the trigger 145. In one embodiment, current will not flow through the return conductor 137 when the trigger closure switch 147 is in an open condition and/or when the toggle switch 143 is in the first configuration, i.e., when the first toggle button 143a is depressed, as described above. In any event, in various circumstances, the current flowing through the tissue T (FIG. 5) from the distal end 152 of the blade 146 to the distal end 153 of the clamp member 151 can treat the tissue positioned intermediate, and/or surrounding, the distal ends 152, 153. In another embodiment, the current may be subtherapeutic for measuring the electrical state of the tissue T (FIG. 5).

The distal end 152 of the blade 146 may comprise a supply electrode while the distal end 153 of the clamp member 151 may comprise a return electrode. In various other embodiments, current can be supplied to the conductor 137 such that the distal end 153 of the clamp member 151 may comprise the supply electrode and the distal end 152 of the blade 146 may comprise the return electrode. In one embodiment, the current can return to the generator 112 via the blade 146, the waveguide 147, and the conductor 139. In either event, referring again to FIG. 1, at least a portion of the return conductor 137 can extend along the outside of the sheath 158, wherein at least another portion of the return conductor 137 can extend through the handpiece assembly 160. In certain embodiments, although not illustrated, at least a portion of the return conductor 137 can be positioned within the sheath 158 and can extend alongside the blade 146.

Figure 6:
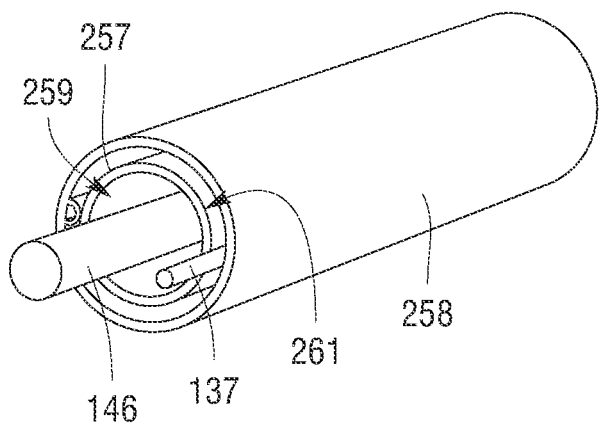
FIG. 6 is a perspective view of an embodiment of a sheath assembly comprising an inner sheath and an outer sheath which can define a first passageway for a waveguide of an ultrasonic instrument and a second passageway for a return conductor.

As shown in FIG. 6, in some embodiments, the surgical instrument 110 may comprise an inner sheath 257 and an outer sheath 258, wherein the inner sheath 257 can define a first, or inner, passageway 259, and wherein the inner sheath 257 and the outer sheath 258 can define a second, or outer, passageway 261 therebetween. In one embodiment, the blade 146 can extend through the inner passageway 259 and the return conductor 137, and/or any other suitable conductor, can extend through the outer passageway 261. In various other embodiments, a conductor can be embedded in at least a portion of the inner sheath 257 or the outer sheath 258.

Figure 7:
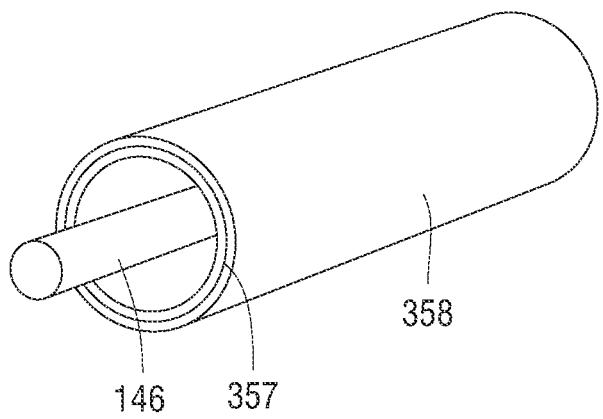
FIG. 7 is a perspective view of an embodiment of a sheath configured to surround at least a portion of a waveguide of an ultrasonic surgical instrument, wherein a conductor can be embedded in at least a portion of a sheath.

As shown in FIG. 7, in one embodiment, a sheath may comprise a non-electrically conductive or insulative material 358, such as plastic and/or rubber, for example, overmolded onto a conductive insert 357, which can be comprised of copper, for example, wherein the conductive insert 357 can allow current flowing through the blade 146 to return to the generator 112 after it has passed through the targeted tissue T (FIG. 5) as described above. In various embodiments, the insulative material 358 can entirely, or at least substantially, surround the conductive insert 357 such that current flowing through the conductive insert 357 does not unintentionally short to non-targeted tissue, for example. In at least one embodiment, the insulative material 358 can cover the inside surface and the outside surface of the conductive insert 357. In certain embodiments, although not illustrated, an insulative material of a sheath may cover only the outer surface of a conductive insert, for example.

In various embodiments, as described above, a first end of the return conductor 137 can be operably coupled to the clamp member 151 such that current can flow therethrough. In certain embodiments, the first end of the return conductor 137 can be soldered and/or welded to the clamp member 151. In one embodiment, although not illustrated, the clamp member 151 may comprise an aperture configured to receive the first end of the return conductor 137 wherein a fastener can be inserted into the aperture in order to secure the first end therein. In at least one such embodiment, the sidewalls of the aperture can be at least partially threaded and the fastener can be threadably received in the threaded aperture.

Figure 8:
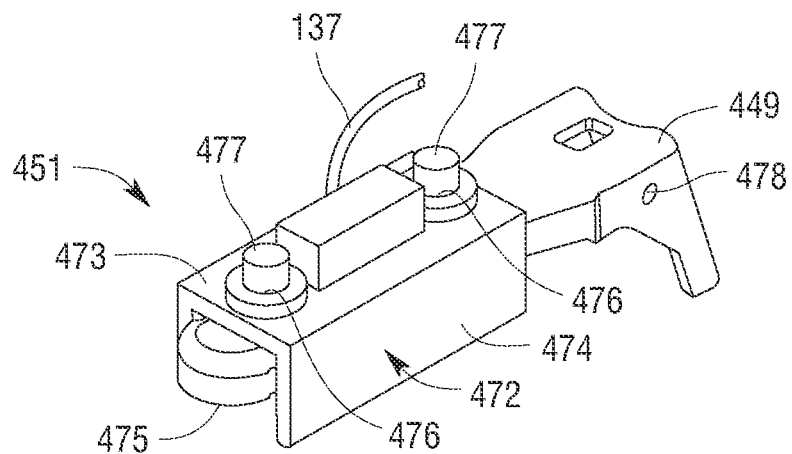
FIG. 8 is a perspective view of an embodiment of a clamp arm assembly configured to hold tissue against a waveguide of an ultrasonic surgical instrument.

As shown in FIG. 8, in one embodiment, a clamp arm assembly 451 may comprise a conductive jacket 472 mounted to a base 449. In one embodiment, the first end of the return conductor 137 may be mounted to the conductive jacket 472 such that current can flow from the blade 146, through tissue positioned intermediate the jacket 472 and the blade 146, and then into the jacket 472 and to the return conductor 137. In various embodiments, the conductive jacket 472 may comprise a center portion 473 and at least one downwardly-extending sidewall 474 which can extend below bottom the surface 475 of the base 449. In the illustrated embodiment, the conductive jacket 472 has two sidewalls 474 extending downwardly on opposite sides of the base 449. In certain embodiments, the center portion 473 may comprise at least one aperture 476 which can be configured to receive a projection 477 extending from the base 449. In one embodiment, the projections 477 can be press-fit within the apertures 476 in order to secure the conductive jacket 472 to the base 449 although, in some embodiments, the projections 477 can be deformed after they have been inserted into the apertures 476. In various embodiments, fasteners can be used to secure the conductive jacket 472 to the base 449.

In various embodiments, the clamp arm assembly 451 may comprise a non-electrically conductive or insulative material, such as plastic and/or rubber, for example, positioned intermediate the conductive jacket 472 and the base 449. The insulative material can prevent current from flowing, or shorting, between the conductive jacket 472 and the base 449. In various embodiments, referring again to FIG. 8, the base 449 may comprise at least one aperture 478, for example, which can be configured to receive a pivot pin (not illustrated), wherein the pivot pin can be configured to pivotably mount the base 449 to the sheath 158, for example, such that the clamp arm assembly 451 can be rotated between open and closed positions relative to the sheath 158. In the embodiment illustrated in FIG. 8, the base 449 includes two apertures 478 positioned on opposite sides of the base 449. In one embodiment, the pivot pin can be comprised of a non-electrically conductive or insulative material, such as plastic and/or rubber, for example, which can be configured to prevent current from flowing into the sheath 158 even if the base 449 is in electrical contact with the conductive jacket 472, for example.

In various embodiments, as described above, the surgical instrument system 110 can be configured such that current can flow from the distal tip of the blade 146, through the tissue T (FIG. 5), and then to the distal tip of the clamp member 151. In one embodiment, as shown in to FIG. 5, the clamp member 151 may comprise a tissue engaging pad or clamp pad 155, for example, mounted thereto, wherein the pad 155 can be configured to contact tissue positioned intermediate the clamp member 151 and the waveguide 146. In one expression of the embodiment, the pad 155 may be formed of a non-electrically conductive or insulative material, such as polytetrafluoroethylene (PTFE), such as for example TEFLON® a trademark name of E. I. Du Pont de Nemours and Company, a low coefficient of friction polymer material, or any other suitable low-friction material. The non-electrically conductive or insulative material can also server to prevent current from flowing between the clamp member 151 and the blade 146 without first passing through the distal end 152 of the blade 146, the targeted tissue T, and the distal end 153 of the clamp member 151. In various embodiments, the pad 155 can be attached to the clamp member 151 utilizing an adhesive, for example. The clamp pad 155 mounts on the clamp member 151 for cooperation with the blade 146, with pivotal movement of the clamp member 151 positioning the clamp pad 155 in substantially parallel relationship to, and in contact with, the blade 146, thereby defining a tissue treatment region. By this construction, tissue is grasped between the clamp pad 155 and the blade 146. The clamp pad 155 may be provided with a non-smooth surface, such as a saw tooth-like configuration to enhance the gripping of tissue in cooperation with the blade 146. The saw tooth-like configuration, or teeth, provide traction against the movement of the blade 146. The teeth also provide counter traction to the blade 146 and clamping movement. It will be appreciated that the saw tooth-like configuration is just one example of many tissue engaging surfaces to prevent movement of the tissue relative to the movement of the blade 146. Other illustrative examples include bumps, criss-cross patterns, tread patterns, a bead, or sand blasted surface.

Figure 9:
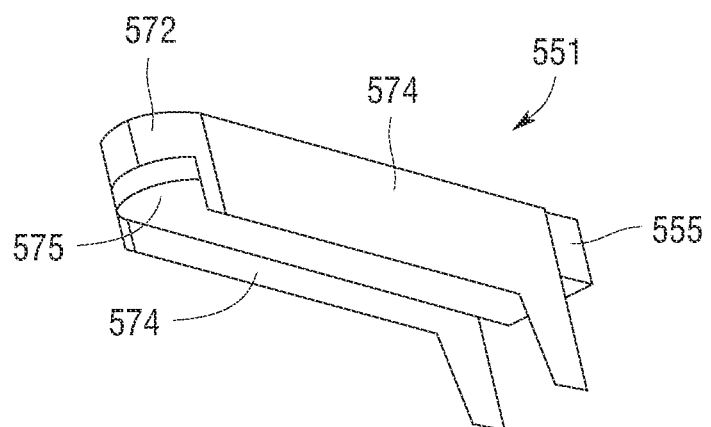
FIG. 9 is a perspective view of another embodiment of a clamp arm assembly having downwardly-extending walls which extend below a tissue-contacting surface.

In various other embodiments, the surgical instrument 110 can be configured such that current can flow through tissue clamped between the blade 146, for example, and the clamp member 151 without having to first pass through the distal ends thereof. In at least one embodiment, referring now to FIG. 9, a clamp arm assembly 551 may comprise an electrically-conductive member 572 and a pad 555 attached thereto, wherein the electrically-conductive member 572 may comprise at least one sidewall 574 extending downwardly therefrom. In one embodiment, current can flow between the blade 146, for example, through tissue positioned between the blade 146 and the sidewalls 574 of the clamp arm assembly 551, and into the sidewalls 574. In various embodiments, gaps can be defined between each sidewall 574 and the blade 146 and, in addition, a gap can be defined between the tissue-contacting surface 575 of the pad 555 and the blade 146.

Figure 10:
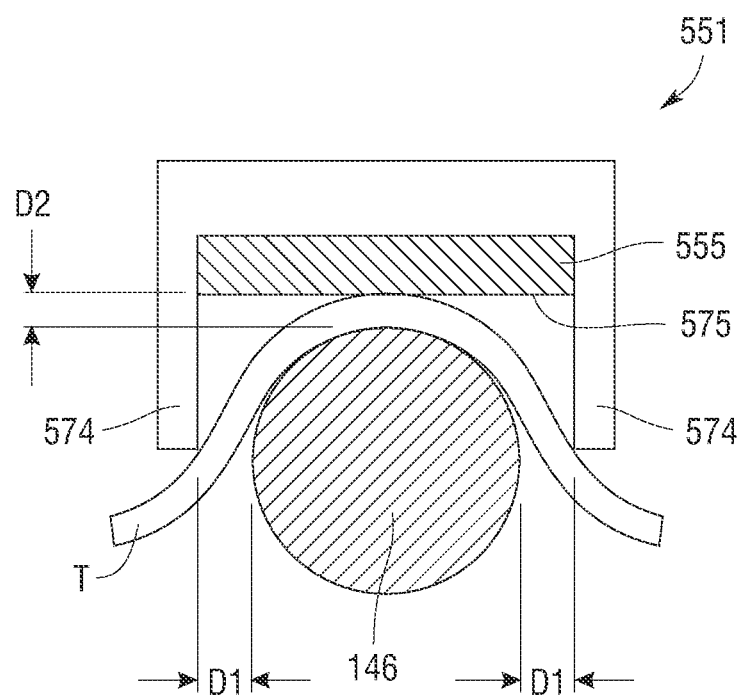
FIG. 10 is a cross-sectional end view of the clamp arm assembly of FIG. 9 positioned in a closed position relative to a waveguide of an ultrasonic surgical instrument.

In one embodiment, referring now to FIG. 10, the gaps between each sidewall 574 and the waveguide 146 can be defined by a distance "D1," wherein the distance D1 can be selected such that, when the clamp arm assembly 551 is positioned in a closed position, the tissue positioned intermediate each of the sidewalls 574 and the blade 146 can be compressed. Although these gaps are illustrated as having the same distance D1, other embodiments are envisioned in which the gaps have different distances. A gap between the tissue-contacting surface 575 and the blade 146 can be defined by a distance "D2," wherein the distance D2 also may be selected such that, when the clamp arm assembly 551 is positioned in a closed position, the tissue-contacting surface 575 can be contact and/or compress the tissue against blade 146.

In various embodiments, a clamp arm assembly may comprise an electrically-conductive pad mounted thereto. In at least one such embodiment, such a pad can be configured to contact and/or compress tissue positioned intermediate the clamp arm assembly and a waveguide, such as the blade 146, for example, such that current can flow from the blade 146 into the pad. In certain embodiments, the electrically conductive pad can be comprised of a typically conductive material, such as copper, for example. In at least one embodiment, the pad can be comprised of a typically non-conductive material, such as PTFE, for example, which can be impregnated with electrically conductive particles, such as medical grade stainless steel, for example, such that the pad is sufficiently conductive to permit current to flow between the blade 146 and the clamp arm.

Figure 11:
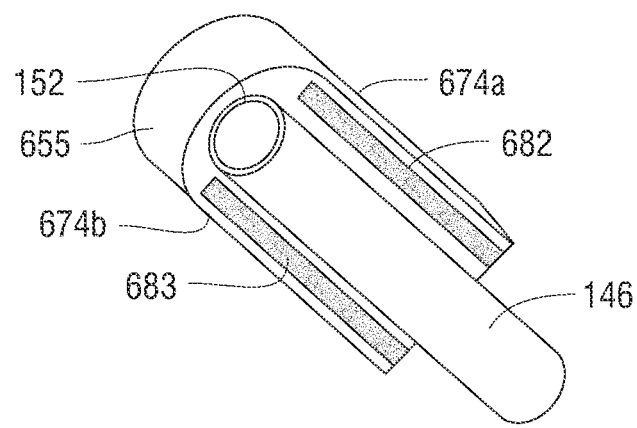
FIG. 11 is a perspective view of a tissue-contacting pad of a clamp arm assembly, wherein the pad includes first and second electrodes embedded therein and positioned relative to a waveguide of an ultrasonic surgical instrument.

In one embodiment, as previously discussed, the surgical instrument 110 comprises the blade 146, for example, which may comprise a first electrode and, in addition, a clamp arm, such as the clamp member 151, for example, which may comprise a second electrode. In various embodiments, as also discussed above, the blade 146 may comprise a supply electrode whereas the clamp member 151 may comprise a return electrode. Alternatively, the clamp member 151 may comprise the supply electrode while the blade 146 may comprise the return electrode. In various other embodiments, a clamp arm may comprise both the supply electrode and the return electrode. In certain embodiments, referring now to FIG. 11, a clamp arm may comprise a pad 655 and two or more electrodes, such as a first electrode 682 and a second electrode 683, for example. In one embodiment, the pad 655 can be comprised of a non-electrically conductive or insulative material, such as PTFE, for example, as previously discussed with reference to the clamp pad 155 (FIG. 5), whereas the electrodes 682, 683 can be comprised of an electrically conductive material, such as copper and/or a PTFE material having electrically conductive particles mixed therein, for example. In various embodiments, the first electrode 682 and/or the second electrode 683 can be embedded within the pad 655. In at least one such embodiment, the pad 655 can be molded onto the electrodes 682, 683 whereas, in certain embodiments, the electrodes 682, 683 can be inserted and/or press-fit into openings formed in the pad 655.

In various embodiments, the first electrode 682 can be positioned adjacent to a first side 674a of the pad 655 while the second electrode 683 can be positioned adjacent to a second side 674b of the pad 655. In use, the first electrode 682 may comprise a supply electrode and the second electrode 683 may comprise a return electrode, wherein current can flow from the supply electrode 682, through tissue clamped or positioned between the pad 655 and the blade 146, for example, and into the return electrode 683. In one embodiment, a supply wire can be operably coupled with the first electrode 682 and a return wire can be operably coupled with the second electrode 683 such that current can be supplied thereto from a power source, such as the generator 112, for example. In various embodiments, referring still to FIG. 11, the electrodes 682, 683 can be positioned within the pad 655 such that the electrodes 682, 683 do not contact the blade 146 when the clamp member 151 (FIG. 5) is in a closed position and short to the blade 146. Although the illustrated embodiment comprises one supply electrode and one return electrode positioned within a pad, embodiments are envisioned in which a pad includes more than one supply electrode and/or more than one return electrode.

Figure 12:
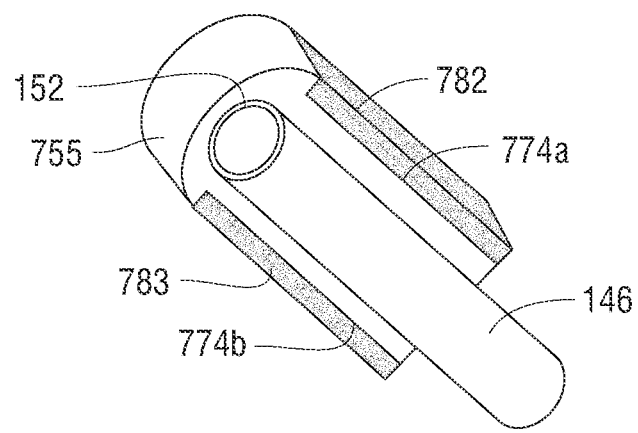
FIG. 12 is a perspective view of another embodiment of a tissue-contacting pad of a clamp arm assembly, wherein the pad includes first and second electrodes mounted thereto and positioned relative to a waveguide of an ultrasonic surgical instrument.

As discussed above, electrodes can be embedded within the pad of a clamp arm assembly. In various embodiments, first and second electrodes can be mounted to the sides of a clamp arm pad. Referring now to FIG. 12, a clamp arm may comprise a pad 755, for example, which can be configured to hold tissue against the blade 146, for example, wherein a first electrode 782 can be mounted to a first side 774a of the pad 755 and wherein a second electrode 783 can be mounted to a second side 774b of the pad 755. In various embodiments, the electrodes 782, 783 can be positioned within cut-outs in the sides of the pad 755 wherein, in certain embodiments, the electrodes 782, 783 can be adhered and/or fastened, for example, to the pad 755. The first electrode 782 may comprise a supply electrode and the second electrode 783 may comprise a return electrode, wherein current can flow from the supply electrode 782, through tissue clamped or positioned between the pad 755 and the blade 146, for example, and into the return electrode 783. In one embodiment, a supply wire can be operably coupled with the first electrode 782 and a return wire can be operably coupled with the second electrode 783 such that current can be supplied thereto from a power source, such as the generator 112, for example. Furthermore, the electrodes 782, 783 can be mounted to the pad 755 such that the electrodes 782, 783 do not contact the blade 146 and create an electrical short thereto. Although the illustrated embodiment comprises one supply electrode and one return electrode mounted to a pad, embodiments are envisioned in which a pad includes more than one supply electrode and/or more than one return electrode.

Figure 13:
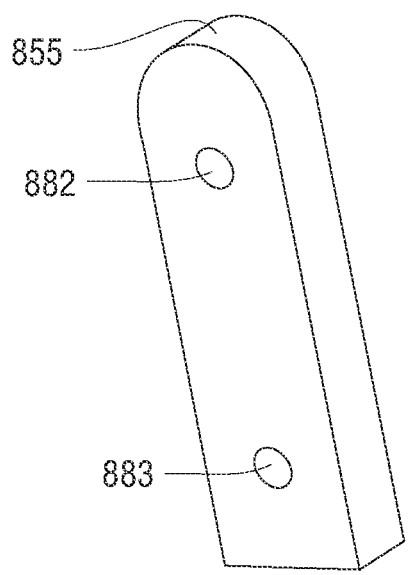
FIG. 13 is a perspective view of another embodiment of a tissue-contacting pad of a clamp arm assembly, wherein the pad includes first and second point electrodes embedded therein.

Still referring to FIG. 12, various electrodes can be configured such that they extend in a longitudinal direction which is parallel, or at least substantially parallel, to the longitudinal axis of the blade 146, for example. In various embodiments, the electrodes can extend along an end effector such that the entire length of the tissue positioned within the end effector can be treated. In various embodiments, referring now to FIG. 13, a clamp arm may comprise a pad 885 having two point electrodes. More particularly, in one embodiment, the pad 855 may comprise a first point electrode 882 and a second point electrode 883 positioned therein, wherein current can flow through tissue positioned intermediate the first point electrode 882 and the second point electrode 883. In at least one such embodiment, the pad 855 can be comprised of a non-electrically conductive material, the first point electrode 882 may comprise a supply electrode, and the second point electrode 883 may comprise a return electrode. In various embodiments, the electrodes 882, 883 can be embedded within the pad 885 and, in one embodiment the pad 885 can be molded around the electrodes 882, 883. In certain embodiments, the electrodes 882, 883 can be inserted into apertures within the pad 855. A supply wire can be operably coupled with the first electrode 882 and a return wire can be operably coupled with the second electrode 883 such that current can be supplied thereto from a power source, such as the generator 112, for example. Furthermore, the electrodes 882, 883 can be positioned within the pad 855 such that the electrodes 882, 883 do not contact the blade 146 and create an electrical short thereto. In one embodiment, the clamp arm supporting pad 885, and/or a sheath rotatably supporting the clamp arm, may further comprise a stop which can be configured to prevent the pad 855 from rotating into a position in which the electrodes 882, 883 contact the blade 146. Although the illustrated embodiment comprises one supply point electrode and one return point electrode positioned within a pad, other embodiments are envisioned in which a pad includes more than one supply point electrode and/or more than one return point electrode. Various embodiments are envisioned in which a pad includes an array of supply point electrodes and/or an array of return point electrodes.

In various embodiments, as described above, a surgical instrument may comprise a clamp arm including both a supply electrode and a return electrode. In one embodiment, the surgical instrument may comprise a waveguide which does not comprise an electrode. In certain embodiments, a supply electrode and a return electrode can be configured such that current can flow therebetween along a predetermined path. In various embodiments, such a path can be one-dimensional. Embodiments having two point electrodes, for example, can permit such a path. In other embodiments, such a path can be two-dimensional. Embodiments having an array of point electrodes, for example, can permit such a path. A two-dimensional path can be referred to as a field. In certain embodiments, a path can be three-dimensional. In at least one such embodiment, a clamp arm assembly can have a supply electrode and a return electrode while the waveguide may comprise one of a supply electrode or a return electrode. In embodiments where the waveguide comprises a return electrode, current can flow from the supply electrode of the clamp arm assembly to the return electrode of the clamp arm assembly and the return electrode of the waveguide. In one such embodiment, the return electrodes may comprise a common ground. In embodiments where the waveguide comprises a supply electrode, current can flow from the waveguide and the supply electrode of the clamp arm assembly to the return electrode of the clamp arm assembly. Such arrangements can permit the current to flow in a three-dimensional path, or field.

Figure 14:
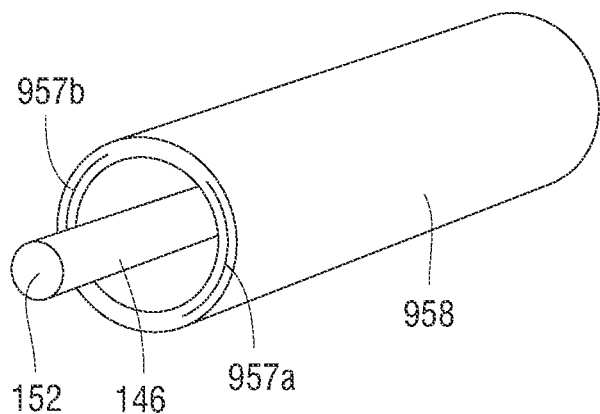
FIG. 14 is a perspective view of an embodiment of a sheath configured to surround at least a portion of a waveguide of an ultrasonic surgical instrument, wherein first and second conductors can be embedded in at least a portion of a sheath.
Figure 15:
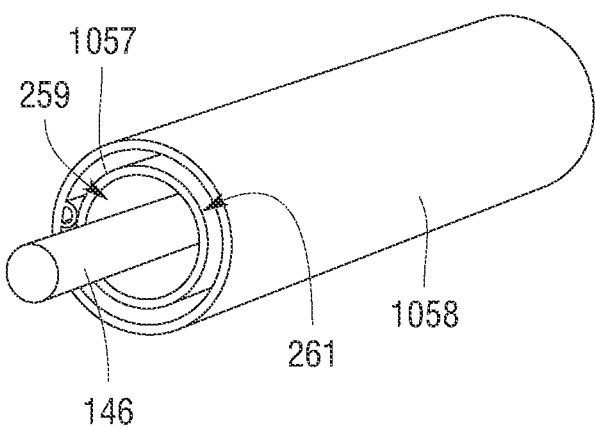
FIG. 15 is a perspective view of an embodiment of a sheath assembly comprising an inner sheath and an outer sheath, wherein the inner sheath and the outer sheath may comprise first and second conductors.

In various embodiments, referring now to FIG. 14, the surgical instrument 110 may comprise a sheath encompassing, or at least partially encompassing, a portion of the blade 146 wherein a sheath may comprise both at least one supply conductor and at least one return conductor. In one embodiment, a sheath may comprise a plurality of conductive inserts, such as a first conductive insert 957a and a second conductive inserts 957b, for example, wherein the first conductive insert 957a may comprise a supply conductor and wherein the second conductive insert 957b may comprise a return conductor. In various embodiments, a non-electrically conductive or insulative material 958, such as plastic and/or rubber, for example, can be overmolded onto the first and second conductive inserts 957a, 957b in order to comprise the sheath. In various other embodiments, the surgical instrument 110 may comprise, referring now to FIG. 15, a sheath assembly encompassing, or at least partially encompassing, a portion of a waveguide wherein the sheath assembly may comprise an inner sheath, such as an inner sheath 1057, for example, and an outer sheath, such as an outer sheath 1058, for example. In one embodiment, the inner sheath 1057 may comprise a supply conductor operably coupled with a supply electrode in a clamp arm assembly, wherein the outer sheath 1058 may comprise a return conductor operably coupled with a return electrode in the clamp arm assembly. In certain embodiments, the inner sheath 1057 and/or the outer sheath 1058 may be comprised of an electrically conductive material, such as medical grade stainless steel, for example, wherein, in one embodiment, one or more surfaces of the inner sheath 1057 and/or the outer sheath 1058 can be coated, or at least partially coated, in a non-conductive material, such as a material comprising poly(p-xylylene) polymers, for example. Materials comprised of poly(p-xylylene) polymers are often sold under the tradename of Parylene™.

Figure 16:
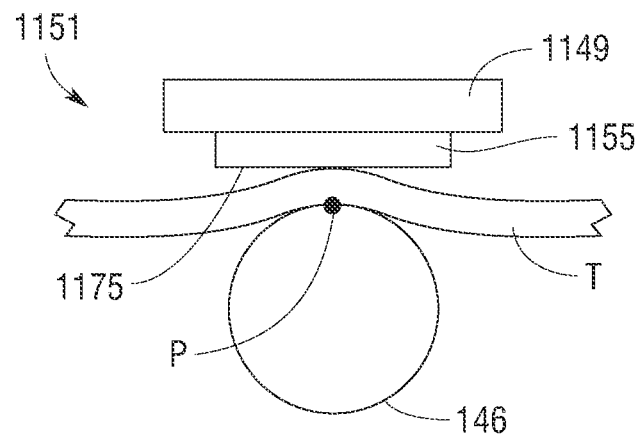
FIG. 16 is an end view of a clamp arm assembly holding tissue against a waveguide.
Figure 17:
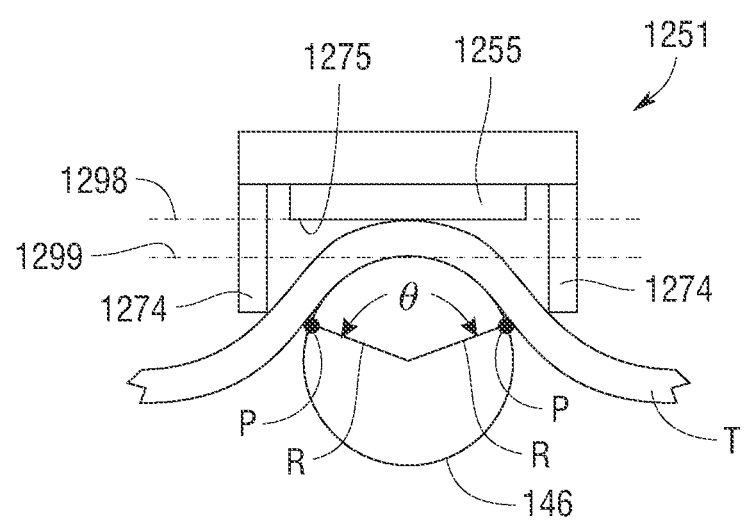
FIG. 17 is an end view of an alternative embodiment of a clamp arm assembly holding tissue against a waveguide.

In various embodiments, a clamp arm can be moved between open and closed positions in order position and/or compress tissue T against a blade. In one embodiment, referring to FIG. 16, a clamp arm 1151 may comprise a base 1149 and a pad 1155 mounted to the base 1149, wherein the pad 1155 can be configured to contact and compress tissue T against the blade 146, for example. As illustrated in FIG. 16, the pad 1155 may comprise a tissue-contacting surface 1175 which, although it may include various serrations, ridges, and/or surface texturing, is planar, or at least substantially planar. In such embodiments, especially when the blade 146 has a round or arcuate cross-section, only a small portion of the tissue T positioned intermediate the blade 146 and the pad 1155 may contact the surface area, or perimeter, of the blade 146. As illustrated in FIG. 16, the tissue T may contact the blade 146 at a contact point P. Various alternative embodiments are envisioned in which the clamp arm 1251, for example, may comprise downwardly-extending sidewalls 1274 which extend below a tissue-contacting surface 1275 of the pad 1255, for example, although a clamp arm may comprise a tissue-contacting surface with or without a pad. In one embodiment, referring to FIG. 17, the sidewalls 1274 can be configured to contact the tissue T positioned laterally with respect to the blade 146 and push the tissue T downwardly. As illustrated in FIG. 17, the sidewalls 1274 can push the tissue T downwardly such that the tissue T positioned intermediate the sidewalls 1274 contacts a larger surface area, or perimeter, on the blade 146 as compared to the embodiment illustrated in FIG. 16. Owing to the larger contact area, the blade 146 may be more efficient in cutting, coagulating, and/or otherwise treating the tissue. In embodiments where the blade 146 may comprise a circular or arcuate cross-section, the perimeter contact distance, i.e., the distance in which the tissue is in contact with the perimeter of the blade 146, may comprise an arclength (s) which can equal the product of the radius of curvature of the arc R and the sweep angle θ defined between the two contact points P. As illustrated in FIG. 17, the contact points P can represent the endpoints of the perimeter in which the tissue T contacts the blade 146. Although the illustrated blade 146 is depicted as having a curved or arcuate cross-section, any other suitable cross-section may be used.

In various embodiments, the tissue-contacting surface 1275 of the clamp arm 1251 can define a plane 1298 which can represent the portions of the pad 1255 which contact the tissue T positioned within the end effector when the clamp arm 1251 is rotated between its open and closed positions. As illustrated in FIG. 17, the sidewalls 1274 of the clamp arm 1251 can extend through the plane 1298, wherein, when the clamp arm 1251 is rotated from an open position into a closed position, the sidewalls 1274 can be positioned laterally along the opposite sides of the blade 146 and, in addition, the tissue-contacting surface 1275 can be positioned against, or adjacent to, the top surface of the blade 146 such that the plane 1298 is aligned with, or respect to, a plane 1299 extending through the top surface of the blade 146. In one embodiment, the plane 1299 can be defined as a tangential plane which is tangential to the perimeter of the blade 146. In one embodiment, the plane 1299 can be tangential to the top tissue-contacting surface of the blade 146, for example, wherein the top tissue-contacting surface of the 146 may comprise the surface closest to the clamp tissue-contacting surface 1275 when the clamp arm 1271 is in its closed position. In the illustrated embodiment, still referring to FIG. 17, the planes 1298, 1299 can be parallel, or at least substantially parallel, to one another when the tissue-contacting surface 1275 is positioned adjacent to the blade 146, while the planes 1298, 1299 can be co-planar, or at least substantially co-planar, with one another when the tissue-contacting surface 1275 is in contact with the blade 146. The sidewalls 1274 can be sized and configured such that they extend through the blade plane 1299 when the clamp arm 1271 is in the closed position. In various embodiments, the sidewalls 1274 may not extend through the plane 1299 when the clamp arm 1251 is in the open position. In one embodiment, the sidewalls 1274 may "break" the plane 1299 as the clamp arm 1251 is being closed, but before it is completely closed. In one embodiment, the sidewalls 1274 may break the plane 1299 just before the clamp arm 1251 reaches its completely closed position.

Figure 18:
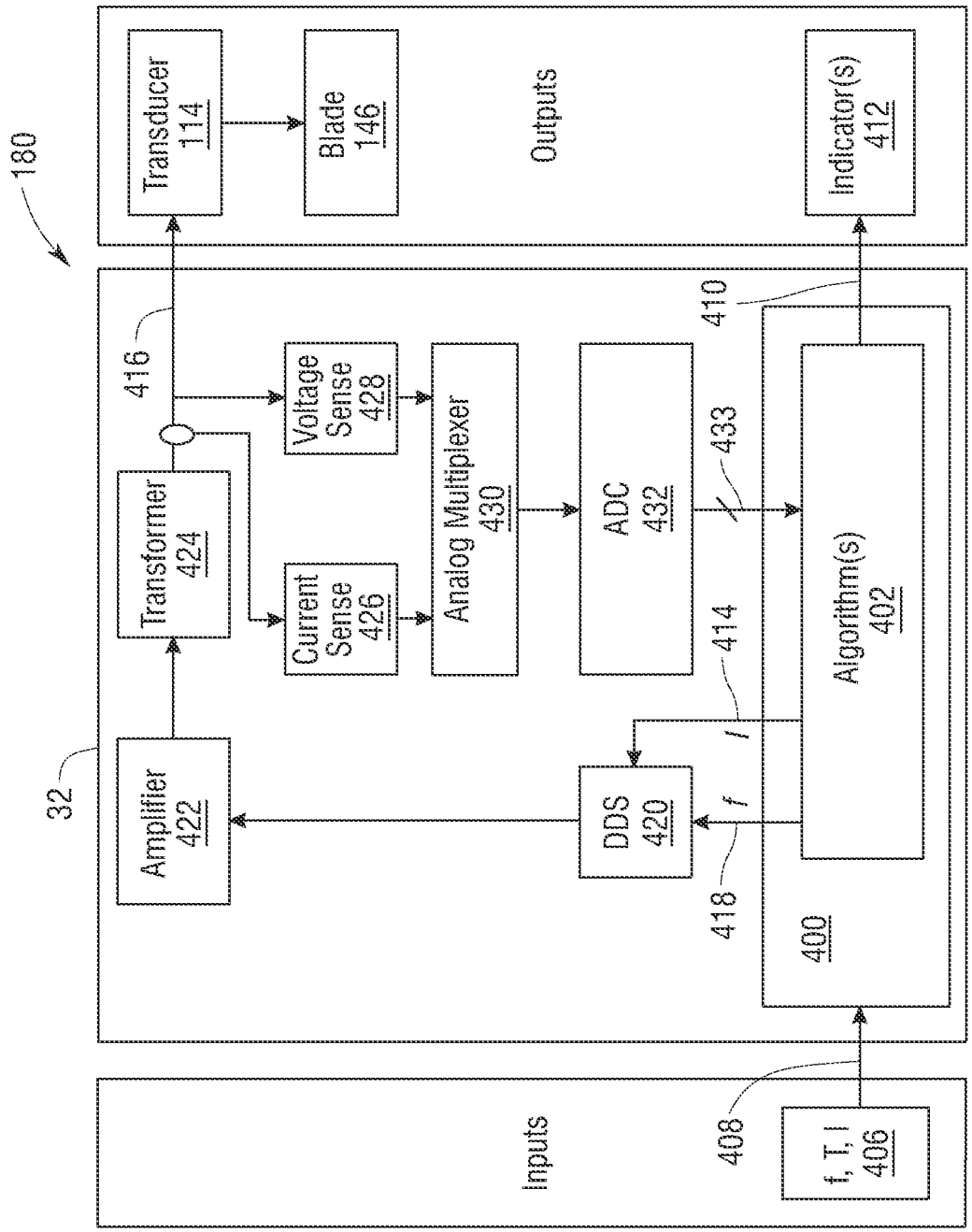
FIG. 18 illustrates one embodiment of a drive system of an ultrasonic generator module, which creates the ultrasonic electrical signal for driving an ultrasonic transducer.

FIG. 18 illustrates one embodiment of a drive system 32 of the ultrasonic generator module 180 shown in FIG. 1, which creates an ultrasonic electrical signal for driving an ultrasonic transducer. With reference now to FIGS. 1 and 18, the drive system 32 is flexible and can create an ultrasonic electrical drive signal 416 at a desired frequency and power level setting for driving the ultrasonic transducer 114. In various embodiments, the generator 112 may comprise several separate functional elements, such as modules and/or blocks. Although certain modules and/or blocks may be described by way of example, it can be appreciated that a greater or lesser number of modules and/or blocks may be used and still fall within the scope of the embodiments. Further, although various embodiments may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In one embodiment, the ultrasonic generator module 180 drive system 32 may comprise one or more embedded applications implemented as firmware, software, hardware, or any combination thereof. The ultrasonic generator module 180 drive system 32 may comprise various executable modules such as software, programs, data, drivers, application program interfaces (APIs), and so forth. The firmware may be stored in nonvolatile memory (NVM), such as in bit-masked read-only memory (ROM) or flash memory. In various implementations, storing the firmware in ROM may preserve flash memory. The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

In one embodiment, the ultrasonic generator module 180 drive system 32 comprises a hardware component implemented as a processor 400 for executing program instructions for monitoring various measurable characteristics of the ultrasonic surgical instrument 110 and generating a corresponding output control signal for operating the surgical instrument 110. In various embodiments, the output control signal is for driving the ultrasonic transducer 114 in cutting and/or coagulation operating modes, measuring electrical characteristics of the surgical instrument 110 and/or the tissue T, and providing feedback to use. It will be appreciated by those skilled in the art that the ultrasonic generator module 180 and the drive system 32 may comprise additional or fewer components and only a simplified version of the ultrasonic generator module 180 and the drive system 32 are described herein for conciseness and clarity. In various embodiments, as previously discussed, the hardware component may be implemented as a DSP, PLD, ASIC, circuits, and/or registers. In one embodiment, the processor 400 may be configured to store and execute computer software program instructions to generate the step function output signals for driving various components of the ultrasonic surgical instrument 110, such as the transducer 114, the end effector 150, and/or the blade 146.

In one embodiment, under control of one or more software program routines, the processor 400 executes the methods in accordance with the described embodiments to perform a variety of functions, such as, for example, generating a step function formed by a stepwise waveform of drive signals comprising current (I), voltage (V), and/or frequency (f) for various time intervals or periods (T), driving the ultrasonic transducer 114, driving the end effector 150 using therapeutic and/or subtherapeutic electrical signals (e.g., RF signal), measuring the impedance (Z) of the transducer 114, measuring the impedance ($Z_t$) of the tissue T, and/or providing feedback to the user. In one embodiment, stepwise waveforms of the drive signals may be generated by forming a piecewise linear combination of constant functions over a plurality of time intervals created by stepping the ultrasonic generator module 180 drive signals, e.g., output drive current (I), voltage (V), and/or frequency (f). The time intervals or periods (T) may be predetermined (e.g., fixed and/or programmed by the user) or may be variable. Variable time intervals may be defined by setting the drive signal to a first value and maintaining the drive signal at that value until a change is detected in a monitored characteristic. Examples of monitored characteristics may comprise, for example, transducer impedance, tissue impedance, tissue heating, tissue transection, tissue coagulation, and the like. The ultrasonic drive signals generated by the ultrasonic generator module 180 include, without limitation, ultrasonic drive signals that excite various vibratory modes of the ultrasonic transducer 114 such as the primary longitudinal mode and harmonics thereof as well flexural and torsional vibratory modes.

In one embodiment, the executable modules comprise one or more algorithm(s) 402 stored in memory that when executed causes the processor 400 to perform a variety of functions, such as, for example, generating a step function formed by a stepwise waveform of drive signals comprising current (I), voltage (V), and/or frequency (f) for various time intervals or periods (T), driving the ultrasonic transducer 114, driving the end effector 150 using a therapeutic and/or subtherapeutic electrical signal (e.g., RF signal), measuring the impedance (Z) of the transducer 114, measuring the impedance ($Z_t$) of the tissue T, and/or providing feedback in accordance with a state of the tissue T. In one embodiment, an algorithm 402 is executed by the processor 400 to generate a step function formed by a stepwise waveform of drive signals comprising current (I), voltage (V), and/or frequency (f) for various time intervals or periods (T). The stepwise waveforms of the drive signals may be generated by forming a piecewise linear combination of constant functions over two or more time intervals created by stepping the generator's 30 output drive current (I), voltage (V), and/or frequency (f). The drive signals may be generated either for predetermined fixed time intervals or periods (T) of time or variable time intervals or periods of time in accordance with the one or more stepped output algorithm(s) 402. Under control of the processor 400, the ultrasonic generator module 180 steps (e.g., increment or decrement) the current (I), voltage (V), and/or frequency (f) up or down at a particular resolution for a predetermined period (T) or until a predetermined condition is detected, such as a change in a monitored characteristic (e.g., transducer impedance, tissue impedance). The steps can change in programmed increments or decrements. If other steps are desired, the ultrasonic generator module 180 can increase or decrease the step adaptively based on measured system characteristics. In other embodiments, algorithms 402 may be executed by the processor 400 to drive the ultrasonic transducer 114, drive the end effector 150 using a therapeutic and/or subtherapeutic electrical signal (e.g., RF signal), measure the impedance (Z) of the transducer 114, measure the impedance ($Z_t$) of the tissue T, and/or to provide feedback in accordance with a state of the tissue T.

In operation, the user can program the operation of the ultrasonic generator module 180 using the input device 406 located on the front panel of the ultrasonic generator module 180 console. The input device 406 may comprise any suitable device that generates signals 408 that can be applied to the processor 400 to control the operation of the ultrasonic generator module 180. In various embodiments, the input device 406 includes buttons, switches, thumbwheels, keyboard, keypad, touch screen monitor, pointing device, remote connection to a general purpose or dedicated computer. In other embodiments, the input device 406 may comprise a suitable user interface. Accordingly, by way of the input device 406, the user can set or program the current (I), voltage (V), frequency (f), and/or period (T) for programming the step function output of the ultrasonic generator module 180. The processor 400 then displays the selected power level by sending a signal on line 410 to an output indicator 412.

In various embodiments, the output indicator 412 may provide visual, audible, and/or tactile feedback to the surgeon to indicate the status of a surgical procedure, such as, for example, when tissue cutting and coagulating is complete based on a measured characteristic of the ultrasonic surgical instrument 110, e.g., transducer impedance, tissue impedance, or other measurements as subsequently described. By way of example, and not limitation, visual feedback comprises any type of visual indication device including incandescent lamps or light emitting diodes (LEDs), graphical user interface, display, analog indicator, digital indicator, bar graph display, digital alphanumeric display. By way of example, and not limitation, audible feedback comprises any type of buzzer, computer generated tone, computerized speech, voice user interface (VUI) to interact with computers through a voice/speech platform. By way of example, and not limitation, tactile feedback comprises any type of vibratory feedback provided through the instrument handpiece assembly 160 or simply housing handle assembly.

In one embodiment, the processor 400 may be configured or programmed to generate a digital current signal 414 and a digital frequency signal 418. These signals 414, 418 are applied to a direct digital synthesizer (DDS) circuit 420 to adjust the amplitude and the frequency (f) of the current output signal 416 to the transducer 114. The output of the DDS circuit 420 is applied to an amplifier 422 whose output is applied to a transformer 424. The output of the transformer 424 is the signal 416 applied to the ultrasonic transducer 114, which is coupled to the blade 146 by way of the waveguide 147.

In one embodiment, the ultrasonic generator module 180 comprises one or more measurement modules or components that may be configured to monitor measurable characteristics of the ultrasonic instrument 110. In embodiment illustrated in FIG. 18, the processor 400 may be employed to monitor and calculate system characteristics. As shown, the processor 400 measures the impedance Z of the transducer 114 by monitoring the current supplied to the transducer 114 and the voltage applied to the transducer 114. In one embodiment, a current sense circuit 426 is employed to sense the current flowing through the transducer 114 and a voltage sense circuit 428 is employed to sense the output voltage applied to the transducer 114. These signals may be applied to the analog-to-digital converter 432 (ADC) via an analog multiplexer 430 circuit or switching circuit arrangement. The analog multiplexer 430 routes the appropriate analog signal to the ADC 432 for conversion. In other embodiments, multiple ADCs 432 may be employed for each measured characteristic instead of the multiplexer 430 circuit. The processor 400 receives the digital output 433 of the ADC 432 and calculates the transducer impedance Z based on the measured values of current and voltage. In response to the transducer impedance (Z), the processor 400 controls the operation of the surgical instrument 110. For example, the processor 400 can adjust the power delivered to the transducer 114, can shut off the power to the transducer 114, and/or provide feedback to the user. In one embodiment, the processor 400 adjusts the output drive signal 416 such that it can generate a desired power versus load curve. In one embodiment, in accordance with a programmed step function algorithms 402, the processor 400 can step the drive signal 416, e.g., the current or frequency, in any suitable increment or decrement in response to the transducer impedance Z.

With reference back now to FIGS. 1 and 18, to actually cause the surgical blade 146 to vibrate, e.g., actuate the blade 146, the user activates the foot switch 144 or the switch 143 on the handpiece assembly 160, as discussed above. This activation outputs the drive signal 416 to the transducer 114 based on programmed values of current (I), frequency (f), and corresponding time periods (T). After a predetermined fixed time period (T), or variable time period based on a measurable system characteristic such as changes in the impedance Z of the transducer 114, the processor 400 changes the output current step or frequency step in accordance with the programmed values. The output indicator 412 communicates the particular state of the process to the user.

The operation of the ultrasonic generator module 180 may be programmed to provide a variety of output drive signals to measure electrical properties of current, voltage, power, impedance, and frequency associated with the transducer 114 in an unloaded state, a lightly loaded state, and a heavily loaded state, for example. When the ultrasonic transducer 114 is in an unloaded state, the ultrasonic generator module 180 output may be stepped in a first sequence, for example. In one embodiment, the ultrasonic generator module 180 is initially activated at about time 0 resulting in a drive current rising to a first set point $I_1$ of about 100 mA. The current is maintained at the first set point $I_1$, for a first period $T_1$. At the end of the first period $T_1$, e.g., about 1 second, the current set point is changed, e.g., stepped, by the ultrasonic generator module 180 in accordance with the software, e.g., the step function algorithm(s) 402, to a second set point $I_2$ of about 175 mA for a second period $T_2$, e.g., about 2 seconds. At the end of the second period $T_2$, e.g., at about 3 seconds, the ultrasonic generator module 180 software changes the current to a third set point $I_3$ of about 350 mA. The voltage, current, power, and frequency respond only slightly because there is no load on the system.

When the ultrasonic transducer 114 is in a lightly loaded state, the ultrasonic generator module 180 is activated at about time 0 resulting in the current rising to the first current set point $I_1$ of about 100 mA. At about 1 second the current set point is changed within the ultrasonic generator module 180 by the software to $I_2$ of about 175 mA, and then again at about 3 seconds the ultrasonic generator module 180 changes the current 300 set point to $I_3$ of about 350 mA. The voltage, current, power, and frequency respond to the light load.

When the ultrasonic transducer 114 is in a heavily loaded state, the ultrasonic generator module 180 is activated at about time 0 resulting in the current rising to the first set point $I_1$ of about 100 mA. At about 1 second the current set point is changed within the ultrasonic generator module 180 by the software to $I_2$ of about 175 mA, and then again at about 3 seconds the ultrasonic generator module 180 changes the current 300 set point to $I_3$ of about 350 mA. The voltage, current, power, and frequency respond to the heavy load.

It will be appreciated by those skilled in the art that the current step function set points (e.g., $I_1$, $I_2$, $I_3$) and the time intervals or periods (e.g., $T_1$, $T_2$) of duration for each of the step function set points described above are not limited to the values described herein and may be adjusted to any suitable value as may be desired for a given set of surgical procedures. Additional or fewer current set points and periods of duration may be selected as may be desired for a given set of design characteristics or performance constraints. As previously discussed, the periods may be predetermined by programming or may be variable based on measurable system characteristics. The embodiments are not limited in this context.

Having described operational details of various embodiments of the surgical system 100, operations for the above surgical system 100 may be further described in terms of a process for cutting and coagulating a blood vessel employing a surgical instrument comprising the input device 406 and the transducer impedance measurement capabilities described with reference to FIG. 18. Although a particular process is described in connection with the operational details, it can be appreciated that the process merely provides an example of how the general functionality described herein can be implemented by the surgical system 100. Further, the given process does not necessarily have to be executed in the order presented herein unless otherwise indicated. As previously discussed, the input device 406 may be employed to program the stepped output (e.g., current, voltage, frequency) to the ultrasonic transducer 114/blade 146 assembly.

Accordingly, one technique for sealing a vessel includes separating and moving the inner muscle layer of the vessel away from the adventitia layer prior to the application of standard ultrasonic energy to transect and seal the vessel. Although conventional methods have achieved this separation by increasing the force applied to the clamp member 151, disclosed is an alternative apparatus and method for cutting and coagulating tissue without relying on clamp force alone. In order to more effectively separate the tissue layers of a vessel, for example, the ultrasonic generator module 180 may be programmed to apply a frequency step function to the ultrasonic transducer 114 to mechanically displace the blade 146 in multiple modes in accordance with the step function. In one embodiment, the frequency step function may be programmed by way of the user interface 406, wherein the user can select a stepped-frequency program, the frequency (f) for each step, and the corresponding time period (T) of duration for each step for which the ultrasonic transducer 114 will be excited. The user may program a complete operational cycle by setting multiple frequencies for multiple periods to perform various surgical procedures.

In one embodiment, a first ultrasonic frequency may be set initially to mechanically separate the muscle tissue layer of a vessel prior to applying a second ultrasonic frequency to cut and seal the vessel. By way of example, and not limitation, in accordance with one implementation of the program, initially, the ultrasonic generator module 180 is programmed to output a first drive frequency $f_1$ for a first period $T_1$ of time (for example less than approximately 1 second), wherein the first frequency $f_1$ is significantly off resonance, for example, $f_o/2$, $2f_o$ or other structural resonant frequencies, where $f_o$ is the resonant frequency (e.g., 55.5 kHz). The first frequency $f_1$ provides a low level of mechanical vibration action to the blade 146 that, in conjunction with the clamp force, mechanically separates the muscle tissue layer (subtherapeutic) of the vessel without causing significant heating that generally occurs at resonance. After the first period $T_1$, the ultrasonic generator module 180 is programmed to automatically switch the drive frequency to the resonant frequency $f_o$ for a second period $T_2$ to transect and seal the vessel. The duration of the second period $T_2$ may be programmed or may be determined by the length of time it actually takes to cut and seal the vessel as determined by the user or may be based on measured system characteristics such as the transducer impedance Z as described in more detail below.

In one embodiment, the tissue/vessel transection process (e.g., separating the muscle layer of the vessel from the adventitia layer and transecting/sealing the vessel) may be automated by sensing the impedance Z characteristics of the transducer 114 to detect when the transection of the tissue/vessel occurs. The impedance Z can be correlated to the transection of the muscle layer and to the transection/sealing of the vessel to provide a trigger for the processor 400 to generate the frequency and/or current step function output. As previously discussed with reference to FIG. 18, the impedance Z of the transducer 114 may be calculated by the processor 400 based on the current flowing through transducer 114 and the voltage applied to the transducer 114 while the blade 146 is under various loads. Because the impedance Z of the transducer 114 is proportional to the load applied to the blade 146, as the load on the blade 146 increases the impedance Z of the transducer 114 increases and as the load on the blade 146 decreases the impedance Z of the transducer 114 decreases. Accordingly, the impedance Z of the transducer 114 can be monitored to detect the transection of the inner muscle tissue layer of the vessel from the adventitia layer and can also be monitored to detect when the vessel has been transected and sealed.

In one embodiment, the ultrasonic surgical instrument 110 may be operated in accordance with a programmed step function algorithm responsive to the transducer impedance Z. In one embodiment, a frequency step function output may be initiated based on a comparison of the transducer impedance Z and one or more predetermined thresholds that have been correlated with tissue loads against the blade 146. When the transducer impedance Z transitions above or below (e.g., crosses) a threshold, the processor 400 applies a digital frequency signal 418 to the DDS circuit 420 to change the frequency of the drive signal 416 by a predetermined step in accordance with the step function algorithm(s) 402 responsive to the transducer impedance Z. In operation, the blade 146 is first located at the tissue treatment site. The processor 400 applies a first digital frequency signal 418 to set a first drive frequency $f_1$ that is off resonance (e.g., $f_o/2$, $2f_o$ or other structural resonant frequencies, where $f_o$ is the resonant frequency). The drive signal 416 is applied to the transducer 114 in response to activation of the switch 312a on the handpiece assembly 160 or the foot switch 434. During this period the ultrasonic transducer 114 mechanically activates the blade 146 at the first drive frequency $f_1$. A force or load may be applied to the clamp member 151 and the blade 146 to facilitate this process. During this period, the processor 400 monitors the transducer impedance Z until the load on the blade 146 changes and the transducer impedance Z crosses a predetermined threshold to indicate that the tissue layer has been transected. The processor 400 then applies a second digital frequency signal 418 to set a second drive frequency $f_2$, e.g., the resonant frequency $f_o$ or other suitable frequency for transecting, coagulating, and sealing tissue. Another portion of the tissue (e.g., the vessel) is then grasped between the clamp member 151 and the blade 146. The transducer 114 is now energized by the drive signal 416 at the second drive frequency $f_2$ by actuating either the foot switch 434 or the switch 312a on the handpiece assembly 160. It will be appreciated by those skilled in the art that the drive current (I) output also may be stepped as described with reference to FIGS. 6-8 based on the transducer impedance Z.

According to one embodiment of a step function algorithm 402, the processor 400 initially sets a first drive frequency $f_1$ that is significantly off resonance to separate the inner muscle layer of the vessel from the adventitia layer. During this period of operation the processor 400 monitors the transducer impedance Z to determine when the inner muscle layer is transected or separated from the adventitia layer. Because the transducer impedance Z is correlated to the load applied to the blade 146, for example, cutting more tissue decrease the load on the blade 146 and the transducer impedance Z. The transection of the inner muscle layer is detected when the transducer impedance Z drops below a predetermined threshold. When the change in transducer impedance Z indicates that the vessel has been separated from the inner muscle layer, the processor 400 sets the drive frequency to the resonant frequency $f_o$. The vessel is then grasped between the blade 146 and the clamp member 151 and the transducer 114 is activated by actuating either the foot switch or the switch on the handpiece assembly 160 to transect and seal the vessel. In one embodiment, the impedance Z change may range between about 1.5 to about 4 times a base impedance measurements from an initial point of contact with the tissue to a point just before the muscle layer is transected and sealed.

Figure 19:
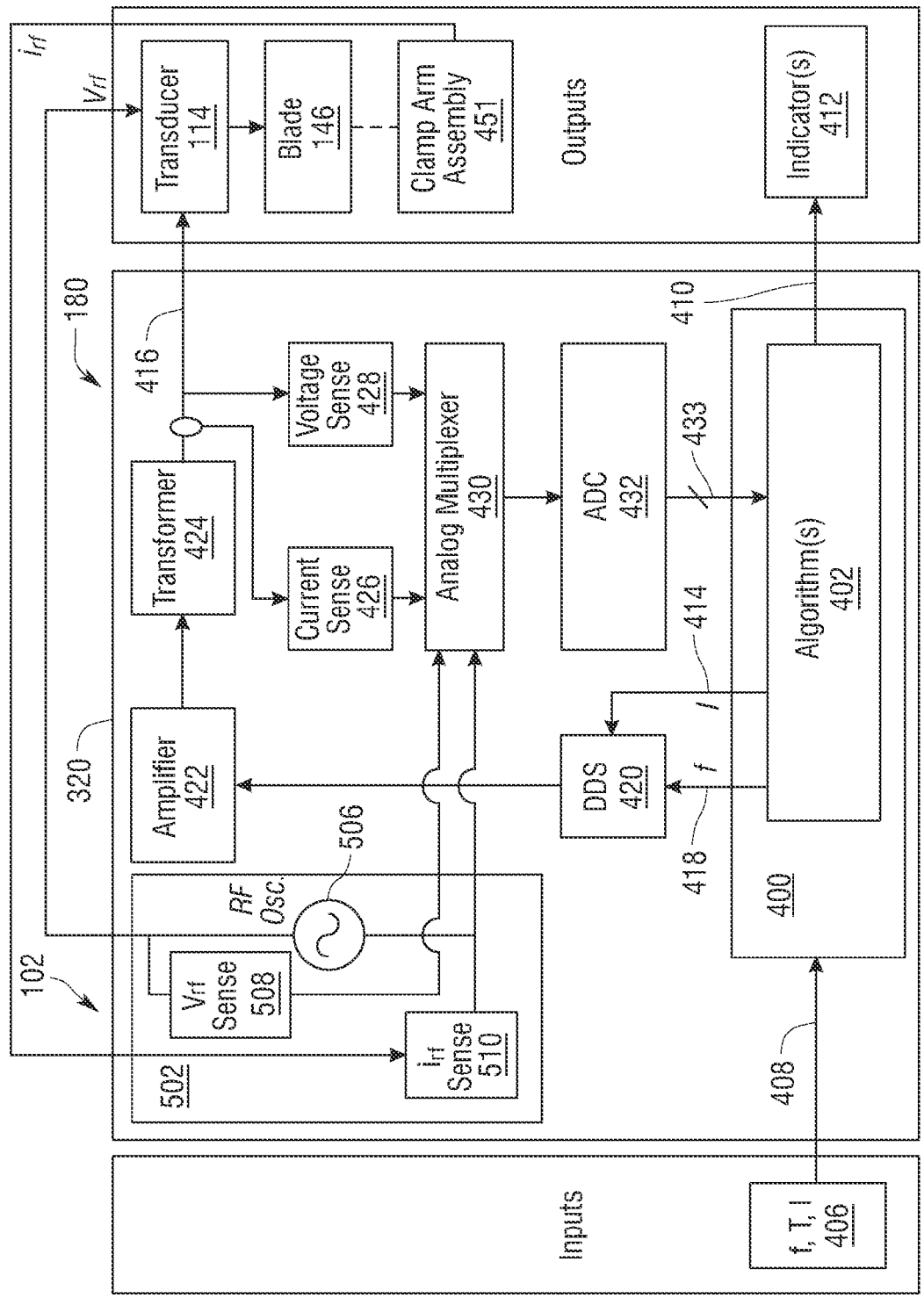
FIG. 19 illustrates one embodiment of a drive system of a generator comprising a tissue impedance module.

With reference now to FIGS. 1, 8, and 19, as previously discussed, in one embodiment, the surgical system 100, and the ultrasonic surgical instrument 110, comprises the signal generator module 102. In one embodiment, the signal generator module 102 may be implemented as a tissue impedance module 502. Although in the presently disclosed embodiment, the signal generator module 102 is shown separate from the surgical instrument 110, in one embodiment, the signal generator module 102 may be formed integrally with the surgical instrument 110, as shown in phantom in FIG. 1, such that the surgical instrument 110 forms a unitary surgical system. In one embodiment, surgical instrument the signal generator module 102 may be configured to monitor the electrical impedance $Z_t$ of the tissue T (FIGS. 5, 10, 16, 17) to control the characteristics of time and power level based on the impedance $Z_t$ of the tissue T. In one embodiment, the tissue impedance $Z_t$ may be determined by applying a subtherapeutic radio frequency (RF) signal to the tissue T and measuring the current through the tissue T by way of a return electrode on the clamp member 151, as previously discussed. In the schematic diagram shown in FIG. 19, an end effector portion of the surgical system 100 comprises the clamp arm assembly 451 (FIG. 8) connected to the distal end of the outer sheath 158. The blade 146 forms a first (e.g., energizing) electrode and the clamp arm assembly 451 comprises an electrically conductive portion that forms a second (e.g., return) electrode. The tissue impedance module 502 is coupled to the blade 146 and the clamp arm assembly 451 through a suitable transmission medium such as a cable 137. The cable 137 comprises multiple electrical conductors for applying a voltage to the tissue T and providing a return path for current flowing through the tissue T back to the impedance module 502. In various embodiments, the tissue impedance module 502 may be formed integrally with the generator 112 or may be provided as a separate circuit coupled to the generator 112 (shown in phantom to illustrate this option).

Still with reference to FIGS. 1, 8, and 19 illustrates one embodiment of an integrated generator module 320 comprising the ultrasonic generator module 180 and the signal generator module 102. As shown, the signal generator module 102 is configured as a tissue impedance module 502. The integrated generator module 320 generates the ultrasonic electrical drive signal 416 to drive the ultrasonic transducer 114. In one embodiment, the tissue impedance module 502 may be configured to measure the impedance $Z_t$ of the tissue T (FIGS. 5, 10, 16, 17) grasped between the blade 146 and the clamp arm assembly 451. The tissue impedance module 502 comprises an RF oscillator 506, a voltage sensing circuit 508, and a current sensing circuit 510. The voltage and current sensing circuits 508, 510 respond to the RF voltage $v_{rf}$ applied to the blade 146 electrode and the RF current $i_{rf}$ flowing through the blade 146 electrode, the tissue, and the conductive portion of the clamp arm assembly 451. The sensed voltage $v_{rf}$ and current $i_{rf}$ are converted to digital form by the ADC 432 via the analog multiplexer 430. The processor 400 receives the digitized output 433 of the ADC 432 and determines the tissue impedance $Z_t$ by calculating the ratio of the RF voltage $v_{rf}$ to current $i_{rf}$ measured by the voltage sense circuit 508 and the current sense circuit 510. In one embodiment, the transection of the inner muscle layer and the tissue may be detected by sensing the tissue impedance $Z_t$. Accordingly, detection of the tissue impedance $Z_t$ may be integrated with an automated process for separating the inner muscle layer from the outer adventitia layer prior to transecting the tissue without causing a significant amount of heating, which normally occurs at resonance. Additional clamp arm and sheath assemblies comprising an electrode as shown in FIGS. 9-17 may be employed without limitation.

Figure 20:
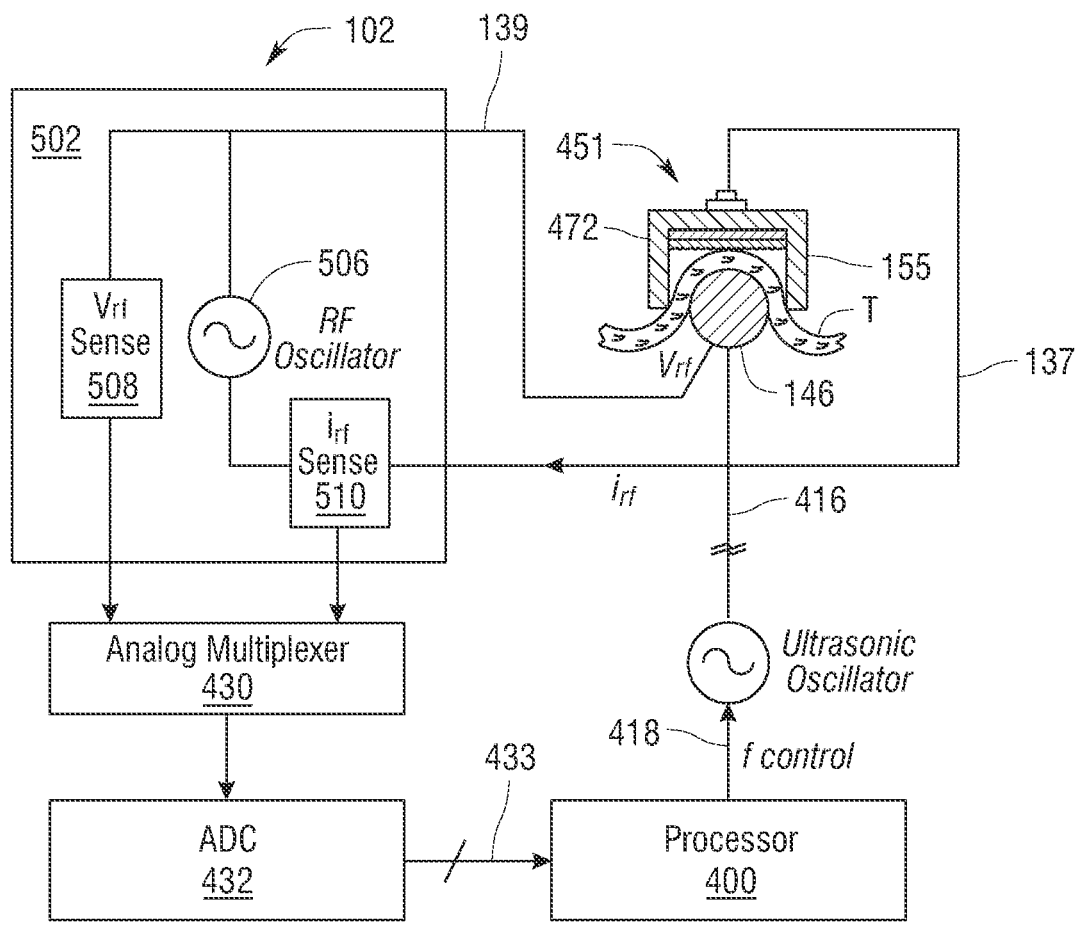
FIG. 20 is a schematic diagram of a tissue impedance module coupled to a blade and a clamp arm assembly with tissue located therebetween.

FIG. 20 is a schematic diagram of the signal generator module 102 configured as the tissue impedance module 502 coupled to the blade 146 and the clamp arm assembly 415 with tissue T located therebetween. With reference now to FIGS. 1, 8, and 18-20, the generator 112 comprises the signal generator module 102 configured as the tissue impedance module 502 configured for monitoring the impedance $Z_t$ of the tissue T located between the blade 146 and the clamp arm assembly 451 during the tissue transection process. The tissue impedance module 502 may is coupled to the ultrasonic surgical instrument 110 by way of the cables 137, 139. The cable includes a first "energizing" conductor 139 connected to the blade 146 (e.g., positive [+] electrode) and a second "return" conductor 137 connected to the conductive jacket 472 (e.g., negative [−] electrode) of the clamp arm assembly 451. In one embodiment, RF voltage $v_{rf}$ is applied to the blade 146 to cause RF current $i_{rf}$ to flow through the tissue T. The second conductor 137 provides the return path for the current $i_{rf}$ back to the tissue impedance module 502. The distal end of the return conductor 137 is connected to the conductive jacket 472 such that the current $i_{rf}$ can flow from the blade 146, through the tissue T positioned intermediate the conductive jacket 472 and the blade 146, and the conductive jacket 472 to the return conductor 137. The impedance module 502 connects in circuit, by way of the first and second conductors 137, 139. In one embodiment, the RF energy may be applied to the blade 146 through the ultrasonic transducer 114 and the waveguide 147. It is worthwhile noting that the RF energy applied to the tissue T for purposes of measuring the tissue impedance $Z_t$ is a low level subtherapeutic signal that does not contribute in a significant manner, or at all, to the treatment of the tissue T.

Having described operational details of various embodiments of the surgical system 100, operations for the above surgical system 100 may be further described with reference to FIGS. 1, 8, and 18-20 in terms of a process for cutting and coagulating a blood vessel employing a surgical instrument comprising the input device 406 and the tissue impedance module 502. Although a particular process is described in connection with the operational details, it can be appreciated that the process merely provides an example of how the general functionality described herein can be implemented by the surgical system 100. Further, the given process does not necessarily have to be executed in the order presented herein unless otherwise indicated. As previously discussed, the input device 406 may be employed to program the step function output (e.g., current, voltage, frequency) to the ultrasonic transducer 114/blade 146 assembly.

In one embodiment, the ultrasonic surgical instrument 110 may be operated in accordance with a programmed step function algorithm 402 responsive to the tissue impedance $Z_t$. In one embodiment, a frequency step function output may be initiated based on a comparison of the tissue impedance $Z_t$ and predetermined thresholds that have been correlated with various tissue states (e.g., desiccation, transection, sealing). When the tissue impedance $Z_t$ transitions above or below (e.g., crosses) a threshold, the processor 400 applies a digital frequency signal 418 to the DDS circuit 420 to change the frequency of an ultrasonic oscillator by a predetermined step in accordance with the step function algorithm 402 responsive to the tissue impedance $Z_t$.

In operation, the blade 146 is located at the tissue treatment site. The tissue T is grasped between the blade 146 and the clamp arm assembly 451 such that the blade 146 and the conductive jacket 472 make electrical contact with the tissue T. The processor 400 applies a first digital frequency signal 418 to set a first drive frequency $f_1$ that is off resonance (e.g., $f_o/2$, $2f_o$ or other structural resonant frequencies, where $f_o$ is the resonant frequency). The blade 146 is electrically energized by the low level subtherapeutic RF voltage $v_{rf}$ supplied by the tissue impedance module 502. The drive signal 416 is applied to the transducer 114/blade 146 in response to actuation of the switch 143 on the handpiece assembly 160 or the foot switch 144434 until the tissue impedance $Z_t$ of the tissue T changes by a predetermined amount. A force or load is then applied to the clamp arm assembly 451 and the blade 146. During this period the ultrasonic transducer 114 mechanically activates the blade 146 at the first drive frequency $f_1$ and as a result, the tissue T begins to desiccate from the ultrasonic action applied between the blade 146 and the one or more clamp pads 155 of the clamp arm assembly 451 causing the impedance $Z_t$ of the tissue T to increase. Eventually, as the tissue T is transected by the ultrasonic action and applied clamp force, the impedance $Z_t$ of the tissue T becomes very high or infinite. It will be appreciated by those skilled in the art that the drive current (I) output also may be stepped as described above based on measured impedance $Z_t$ of the tissue T.

In one embodiment, the impedance $Z_t$ of tissue T may be monitored by the impedance module 502 in accordance with the following process. A measurable RF current $i_1$ is conveyed through the first energizing conductor 139 to the blade 146, through the tissue T, and back to the impedance module 502 through the conductive jacket 472 and the second conductor 137. As the tissue T is desiccated and cut by the ultrasonic action of the blade 146 acting against the one or more clamp pads 155, the impedance of the tissue 514 increases and thus the current $i_1$ in the return path, i.e., the second conductor 137, decreases. The impedance module 502 measures the tissue impedance $Z_t$ and conveys a representative signal to the ADC 432 whose digital output 433 is provided to the processor 400. The processor 400 calculates the tissue impedance $Z_t$ based on these measured values of $v_{rf}$ and $i_{rf}$. In response to the transducer impedance $(Z_t)$, the processor 400 controls the operation of the surgical instrument 110. For example, the processor 400 can adjust the power delivered to the transducer 114, can shut off the power to the transducer 114, and/or provide feedback to the user. In one embodiment, the processor 400 steps the frequency by any suitable increment or decrement in response to changes in the impedance $Z_t$ of the tissue T. In other embodiments, the processor 400 controls the drive signals 416 and can make any necessary adjustments in amplitude and frequency in response to the tissue impedance $Z_t$. In one embodiment, the processor 400 can cut off the drive signal 416 when the tissue impedance $Z_t$ reaches a predetermined threshold value.

Accordingly, by way of example, and not limitation, in one embodiment, the ultrasonic surgical instrument 110 may be operated in accordance with a programmed stepped output algorithm to separate the inner muscle layer of a vessel from the adventitia layer prior to transecting and sealing the vessel. As previously discussed, according to one step function algorithm, the processor 400 initially sets a first drive frequency $f_1$ that is significantly off resonance. The transducer 114 is activated to separate the inner muscle layer of the vessel from the adventitia layer and the tissue impedance module 502 applies a subtherapeutic RF voltage $v_{rf}$ signal to the blade 146. During this period $T_1$ of operation the processor 400 monitors the tissue impedance $Z_t$ to determine when the inner muscle layer is transected or separated from the adventitia layer. The tissue impedance $Z_t$ is correlated to the load applied to the blade 146, for example, when the tissue becomes desiccated or when the tissue is transected the tissue impedance $Z_t$ becomes extremely high or infinite. The change in tissue impedance $Z_t$ indicates that the vessel has been separated or transected from the inner muscle layer and the generator 112 is deactivated for a second period of time $T_2$. The processor 400 then sets the drive frequency to the resonant frequency $f_o$. The vessel is then grasped between the blade 146 and the clamp arm assembly 451 and the transducer 114 is reactivated to transect and seal the vessel. Continuous monitoring of the tissue impedance $Z_t$ provides an indication of when the vessel is transected and sealed. Also, the tissue impedance $Z_t$ may be monitored to provide an indication of the completeness of the tissue cutting and/or coagulating process or to stop the activation of the generator 112 and/or the ultrasonic generator module 180 when the impedance $Z_t$ of the tissue T reaches a predetermined threshold value. The threshold for the tissue impedance $Z_t$ may be selected, for example, to indicate that the vessel has been transected. In one embodiment, the tissue impedance $Z_t$ may range between about 10 Ohms to about 1000 Ohms from an initial point to a point just before the muscle layer is transected and sealed.

The applicants have discovered that experiments that run varying current set points (both increasing and decreasing) and dwell times indicate that the described embodiments can be used to separate the inner muscle layer from the outer adventitia layer prior to completing the transection resulting in improved hemostasis and potentially lower total energy (heat) at the transection site. Furthermore, although the surgical instrument 110 has been described in regards to impedance threshold detection schemes to determine when the muscle layer is separated from the adventitia, other embodiments that do not employ any detection scheme are within the scope of the present disclosure. For example, embodiments of the surgical instrument 110 may be employed in simplified surgical systems wherein non-resonant power is applied to separate the layers for a predetermined time of approximately 1 second or less, prior to applying a resonant power to cut the tissue. The embodiments are not limited in this context.

In various embodiments, the surgical instrument 110 may be programmed for detecting a change of state of tissue being manipulated by an ultrasonic surgical instrument and providing feedback to the user to indicate that the tissue has undergone such change of state or that there is a high likelihood that the tissue has undergone such change of state. As used herein, the tissue may undergo a change of state when the tissue is separated from other layers of tissue or bone, when the tissue is cut or transected, when the tissue is coagulated, and so forth while being manipulated with an end effector of an ultrasonic surgical instrument, such as, for example, the end effector 150 of the ultrasonic surgical instrument 110. A change in tissue state may be determined based on the likelihood of an occurrence of a tissue separation event.

With reference to FIGS. 1, 5, and 18-20, in various embodiments, the impedance Z and the tissue $Z_t$, as well as any other suitable electrical measurements, that can be made with the surgical system 100, may be used to provide feedback by the output indicator 412 shown in FIGS. 18 and 19. The output indicator 412 is particularly useful in applications where the tissue being manipulated by the end effector 151 is out of the user's field of view and the user cannot see when a change of state occurs in the tissue T. The output indicator 412 communicates to the user that a change in tissue state has occurred as determined in accordance with the operations described with respect to various logic flows. As previously discussed, the output indicator 412 may be configured to provide various types of feedback to the user including, without limitation, visual, audible, and/or tactile feedback to indicate to the user (e.g., surgeon, clinician) that the tissue has undergone a change of state of the tissue. By way of example, and not limitation, as previously discussed, visual feedback comprises any type of visual indication device including incandescent lamps or LEDs, graphical user interface, display, analog indicator, digital indicator, bar graph display, digital alphanumeric display. By way of example, and not limitation, audible feedback comprises any type of buzzer, computer generated tone, computerized speech, VUI to interact with computers through a voice/speech platform. By way of example, and not limitation, tactile feedback comprises any type of vibratory feedback provided through the instrument housing handpiece assembly 160.

The processor 400 to determines a change in tissue state in accordance with the operations described above and provides feedback to the user by way of the output indicator 412. The processor 400 monitors and evaluates the voltage, current, and/or frequency signal samples available from the generator 32, 320 and according to the evaluation of such signal samples determines whether a change in tissue state has occurred. A change in tissue state may be determined based on the type of ultrasonic instrument and the power level that the instrument is energized at. In response to the feedback, the operational mode of the ultrasonic surgical instrument 110 may be controlled by the user or may be automatically or semi-automatically controlled.

In one embodiment, the processor 400 portion of the drive system 32, 320 samples the voltage (v), current (i), and frequency (f) signals of the ultrasonic generator module 180 and/or the signal generator module 102. As previously discussed, the output indicator 412 may provide visual, audible, and/or tactile feedback to alert the user of the ultrasonic surgical instrument 110 that a change in tissue state has occurred. In various embodiments, in response to the feedback from the output indicator 412, the operational modes of the generator 112, the ultrasonic generator module 180, the signal generator module 102, and/or the ultrasonic instrument 110 may be controlled manually, automatically, or semi-automatically. The operational modes include, without limitation, disconnecting or shutting down the output power, reducing the output power, cycling the output power, pulsing the output power, and/or outputting momentary surge of high-power. In one embodiment, the operational modes include, operating the surgical instrument 110 in a first operating mode in which the transducer 14 produces mechanical energy, or vibrations, that are transmitted to the end effector 151 and a second operating mode in which electrical energy, or current, can flow through the end effector 151 to perform electrosurgery. The operational modes of the ultrasonic instrument 110 in response to the change in tissue state can be selected, for example, to minimize heating effects of the end effector 151, e.g., of the clamp pad 155, to prevent or minimize possible damage to the surgical instrument 110, and/or surrounding tissue. This is advantageous because heat is generated exponentially when the transducer 114 is activated with nothing between the jaws of the end effector 151 as is the case when a change in tissue state occurs.

In various embodiments, the change of state of the tissue may be determined based on transducer and tissue impedance measurements as previously described, or based on voltage, current, and frequency measurements in accordance with the operations described in the disclosure of the following commonly-owned, contemporaneously-filed U.S. patent application, which is incorporated herein by reference in its entirety: U.S. patent application Ser. No. 12/503,775, entitled "ULTRASONIC DEVICE FOR CUTTING AND COAGULATING WITH STEPPED OUTPUT," now U.S. Pat. No. 8,058,771.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Sterilization can also be done by any number of ways known to those skilled in the art including beta or gamma radiation, ethylene oxide, and/or steam.

In various embodiments, an ultrasonic surgical instrument can be supplied to a surgeon with a waveguide and/or end effector already operably coupled with a transducer of the surgical instrument. In at least one such embodiment, the surgeon, or other clinician, can remove the ultrasonic surgical instrument from a sterilized package, plug the ultrasonic instrument into a generator, as outlined above, and use the ultrasonic instrument during a surgical procedure. Such a system can obviate the need for a surgeon, or other clinician, to assemble a waveguide and/or end effector to the ultrasonic surgical instrument. After the ultrasonic surgical instrument has been used, the surgeon, or other clinician, can place the ultrasonic instrument into a sealable package, wherein the package can be transported to a sterilization facility. At the sterilization facility, the ultrasonic instrument can be disinfected, wherein any expended parts can be discarded and replaced while any reusable parts can be sterilized and used once again. Thereafter, the ultrasonic instrument can be reassembled, tested, placed into a sterile package, and/or sterilized after being placed into a package. Once sterilized, the reprocessed ultrasonic surgical instrument can be used once again.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument comprising:
a housing;
a generator supported by said housing, said generator to generate an ultrasonic drive signal;
an electrical contact assembly in electrical communication with said generator;
an acoustic assembly comprising first and second piezoelectric elements, said acoustic assembly rotatable with respect to said generator and said electrical contact assembly, wherein said electrical contact assembly is in electrical communication with said first and second piezoelectric elements, wherein said acoustic assembly comprises a first electrode supported for continuous rotational contact with said electrical contact assembly; and
a waveguide operably connected to said acoustic assembly, said waveguide rotatable with respect to said housing and said generator.

2. The surgical instrument of claim 1 wherein said electrical contact assembly comprises:

a first slip ring contact in continuous rotational contact with said first electrode.

3. The surgical instrument of claim 1 wherein said first and second piezoelectric elements have a first circumference and wherein said first electrode has an annular shape with a second circumference that is greater than said first circumference.

4. The surgical instrument of claim 3 wherein said first and second piezoelectric elements are acoustically coupled to first and second resonators.

5. The surgical instrument of claim 4 wherein said second resonator rotatably interfaces with said waveguide operably attached to an end effector.

6. The surgical instrument of claim 5 wherein said waveguide is rotatably supported by said housing to enable said waveguide to be selectively rotated relative to said housing and said second resonator.

7. The surgical instrument of claim 5 wherein said waveguide is coupled to a rotation wheel rotatably supported by said housing.

8. The surgical instrument of claim 1 wherein said generator is configured to generate a radio frequency signal.

9. The surgical instrument of claim 1 further comprising an end effector acoustically coupled to said acoustical assembly.

10. The surgical instrument of claim 9 wherein said end effector has a movable portion thereon and wherein said surgical instrument comprises a trigger portion operably supported on said housing and communicating with said movable portion of said end effector for selectively actuating said movable portion.

11. The surgical instrument of claim 10 wherein said housing has a pistol grip portion.

12. The surgical instrument of claim 1 wherein said generator comprises an ultrasonic generator module to generate the ultrasonic drive signal.

13. The surgical instrument of claim 1 wherein said generator comprises a signal generator module to generate a radio frequency signal.

14. The surgical instrument of claim 1 wherein said acoustic assembly comprises:
a second electrode supported for continuous rotational contact with said electrical contact assembly.

15. The surgical instrument of claim 14 wherein said electrical contact assembly comprises:
a second slip ring contact in continuous rotational contact with said second electrode.

16. A surgical instrument comprising:
a housing;
generator means supported by said housing, said generator means to generate an ultrasonic drive signal;
acoustic means comprising first and second piezoelectric means to generate ultrasonic motions upon application of said ultrasonic drive signal thereto, said acoustic means rotatable with respect to said generator means;
waveguide means rotatably coupled with said acoustic means;
signal means to supply said ultrasonic drive signal to said acoustic means, wherein said signal means is located between said first and second piezoelectric means, wherein said acoustic means comprises a first electrode supported for continuous rotational contact with said signal means; and
coupling means coupled to said acoustic means and said signal means to transit said ultrasonic drive signal from said signal means to said acoustic means.

17. The surgical instrument of claim 16 wherein said waveguide means is to transmit said ultrasonic motions from said acoustic means to a surgical end effector operably coupled to said waveguide means.

18. The surgical instrument of claim 16 wherein said acoustic means comprises:
a second electrode supported for continuous rotational contact with said signal means.

19. The surgical instrument of claim 18 wherein said signal means comprises:
a second slip ring contact in continuous rotational contact with said second electrode.

20. A surgical instrument system comprising:
a housing;
a generator supported by said housing;
an acoustic assembly rotatably supported by said housing for rotatable travel relative thereto, said acoustic assembly rotatable with respect to said generator, said acoustic assembly configured to generate ultrasonic motions upon application of an ultrasonic drive signal thereto;
a waveguide rotatably supported by said housing in rotatable contact with said acoustic assembly;
an end effector operably coupled to said waveguide;
a signal source for generating a radio frequency signal; and
an electrical contact assembly supported within said housing and in electrical contact with said signal source and said acoustic assembly, wherein said acoustic assembly comprises a first electrode supported for continuous rotational contact with said electrical contact assembly.

21. The surgical instrument of claim 20 wherein said acoustic assembly comprises:
a second electrode supported for continuous rotational contact with said electrical contact assembly.

22. The surgical instrument of claim 21 wherein said electrical contact assembly comprises:
a second slip ring contact in continuous rotational contact with said second electrode.

23. A surgical instrument comprising:
a housing;
a generator supported by said housing, said generator to generate an ultrasonic drive signal;
an electrical contact assembly in electrical communication with said generator;
an acoustic assembly comprising first and second piezoelectric elements, said acoustic assembly rotatable with respect to said generator and said electrical contact assembly, wherein said electrical contact assembly is in electrical communication with said first and second piezoelectric elements, wherein said acoustic assembly comprises a first electrode supported for continuous rotational contact with said electrical contact assembly; and
a waveguide operably connected to said acoustic assembly, said waveguide rotatable with respect to said housing and said generator;
wherein said first and second piezoelectric elements are acoustically coupled to first and second resonators.

* * * * *